United States Patent
Argentine

(10) Patent No.: US 10,517,711 B2
(45) Date of Patent: Dec. 31, 2019

(54) DISSECTION PROSTHESIS SYSTEM AND METHOD

(71) Applicant: Medtronic Vascular, Inc., Santa Rosa, CA (US)

(72) Inventor: Jeffery Argentine, Petaluma, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 647 days.

(21) Appl. No.: 15/137,107

(22) Filed: Apr. 25, 2016

(65) Prior Publication Data
US 2017/0304041 A1  Oct. 26, 2017

(51) Int. Cl.
*A61F 2/07* (2013.01)
*A61F 2/89* (2013.01)

(52) U.S. Cl.
CPC ............. *A61F 2/07* (2013.01); *A61F 2/89* (2013.01); *A61F 2230/0069* (2013.01)

(58) Field of Classification Search
CPC ...... A61F 2/852; A61F 2/07; A61F 2002/821; A61F 2002/075; A61F 2002/061
See application file for complete search history.

(56) References Cited

U.S. PATENT DOCUMENTS 6,270,524 B1 * 8/2001 Kim .................... A61F 2/91
                                                   606/194
6,613,078 B1    9/2003 Barone
8,292,949 B2   10/2012 Berra et al.
8,663,310 B2    3/2014 Greenberg et al.
8,945,203 B2 * 2/2015 Shalev ................. A61F 2/07
                                                   623/1.13
2003/0074049 A1  4/2003 Hoganson et al.
2004/0176832 A1  9/2004 Hartley et al.
2008/0119943 A1  5/2008 Armstrong et al.
(Continued)

FOREIGN PATENT DOCUMENTS

CN    204158523    2/2015
EP    0893108      1/1999
(Continued)

OTHER PUBLICATIONS

Akin et al., "Thoracic Endovascular Stent-Graft Therapy in Aortic Dissection", Cardiology Nov. 2010, vol. 25, Issue 6, pp. 552-559.
(Continued)

*Primary Examiner* — Julie A Szpira

(57) ABSTRACT

A dissection prosthesis system for implantation within a blood vessel includes a first prosthesis and a second prosthesis. The first prosthesis includes a first stent ring, a second stent ring, a first graft material band coupling the first stent ring to the second stent ring, a third stent ring, and a second graft material band coupling the second stent ring to the third stent ring. The second stent ring includes a plurality of openings that enable fluid flow from a lumen of the first prosthesis through the plurality of openings. The graft material bands may include band openings disposed therethrough to enable fluid flow from the lumen through the band openings. The second prosthesis includes a stent coupled to a graft material. The second prosthesis is configured to be disposed within the lumen of the first prosthesis.

14 Claims, 21 Drawing Sheets

(56) References Cited

U.S. PATENT DOCUMENTS

| | | |
|---|---|---|
| 2009/0171437 A1 | 7/2009 | Brocker et al. |
| 2010/0087907 A1 | 4/2010 | Lattouf |
| 2011/0118816 A1 | 5/2011 | Jensen et al. |
| 2011/0202075 A1* | 8/2011 | Feng .................. A61F 2/064 606/151 |
| 2014/0277338 A1 | 9/2014 | Kolbel et al. |
| 2018/0021158 A1* | 1/2018 | Davis .................. A61F 2/07 623/1.12 |

FOREIGN PATENT DOCUMENTS

| | | |
|---|---|---|
| GB | 2516928 | 2/2015 |
| WO | WO96/21404 | 7/1996 |
| WO | WO2002024247 | 3/2002 |
| WO | WO2008091925 | 7/2008 |
| WO | WO2009/145901 | 12/2009 |
| WO | WO2011/081814 | 7/2011 |

OTHER PUBLICATIONS

PCT/US2017/027049, The International Search Report and the Written Opinion of the International Searching Authority, dated Jun. 28, 2017, 16pgs.

* cited by examiner

DISSECTION PROSTHESIS SYSTEM AND METHOD

FIELD OF THE INVENTION

The present invention relates to a system and method for the treatment of an aortic dissection. More particularly, the present invention relates to a stent-graft prosthesis system for treatment of an aortic dissection wherein blood flow to branch arteries is maintained.

BACKGROUND

An aortic dissection is a condition wherein the inner layer of the aorta tears causing the inner and outer layers of the aortic wall to separate, or dissect. Blood, under pressure, flows into the tear further separating and expanding the inner and outer aortic wall into an inflated sack known as a false lumen.

Treatment of an aortic dissection depends on the location of the dissection (ascending aorta, aortic arch, or descending aorta) and may include surgery and/or medication. Traditional open surgery inflicts significant patient trauma and discomfort, requires extensive recuperation times, and may result in life-threatening complications. Medication treatment may not be sufficient in some cases. For example, and not by way of limitation, malperfusion syndrome is a complication of aortic dissection cased by branch-vessel involvement resulting in end-organ ischaemic dysfunction. Malperfusion syndrome is one trigger for endovascular treatment. Malperfusion syndrome may be static or dynamic and result in loss of blood supply to critical organs.

To address these concerns, efforts have been made to perform aortic dissection repair using minimally invasive techniques including percutaneous transcatheter (or transluminal) delivery and implantation of a stent-graft prosthesis at a treatment site. In such methods, a stent-graft prosthesis is compacted for delivery in a catheter and then advanced, for example through the femoral artery, and through the vascular to the treatment site within the aorta. A stent-graft prosthesis is generally a stent coupled to a graft material. While stent-graft prostheses are generally considered endovascular devices, there is a developing theory encompassing a hybrid procedure wherein endovascular devices can be used in conjunction with traditional open surgical procedures.

FIGS. 1-2 illustrate an aorta 100 with an aortic dissection 102 and treatment thereof using a conventional stent-graft prosthesis 200. The aorta includes an ascending aorta 106, an aortic arch 108, and a descending aorta 110, as shown in FIG. 1. The aortic arch 108 includes a plurality of branch arteries including the innominate artery 112, the left common carotid artery 114, and the left subclavian artery 116. The descending aorta 110 includes a plurality of branch and ancillary arteries such as, but not limited to the renal arteries (not shown in FIGS. 1-3), superior mesenteric artery (SMA) (not shown in FIGS. 1-3), intercostal arteries 120 and subcostal arteries 122, providing first blood flow BF1 to bodily organs including, but not limited to the abdominal muscles, spine, intestines, kidneys, bowels, and legs (not shown in FIGS. 1-3). While FIG. 1-2 shows only intercostal artery 120 and subcostal artery 122, this is for illustrative purposes only and intercostal arteries 120 and subcostal arteries 122 each represent a plurality of arteries. In the exemplary aortic dissection 102 shown in FIG. 1, the wall of the descending aorta 110 may be injured so that a tear 124 in an inner aortic wall 126 occurs, as shown in FIG. 1.

Blood, under pressure from the heart, flows into tear 124, as shown by third blood flow BF3, and splits, or dissects inner aortic wall 126 from outer aortic wall 128, forming a false lumen 130. False lumen 130 and blood therein under pressure forces inner aortic wall 126 towards a centerline $CL_d$ of descending aorta 110 such that blood flow in natural lumen 132 of descending aorta 110 is restricted/reduced. False lumen 130 and blood therein under pressure forces outer aortic wall 128 away from centerline $CL_d$ of descending aorta 110, causing a point of potential aneurysm, as shown in FIG. 1. A normal aortic wall position 134 is shown in FIG. 1 as a dotted line.

Treatment of aortic dissection 102 of aorta 100 requires that tear 124 be closed off such that false lumen 130 is isolated or depressurized. A conventional stent-graft prosthesis 200 is deployed at the site of aortic dissection 102 as shown in FIG. 2. Prosthesis 200 includes a stent frame 202, also known as a stent or stent ring, and a graft material 204. When stent-graft prosthesis 200 is deployed at aortic dissection 102 and in a radially expanded deployed configuration, a first outward radial force OF1 of stent-graft prosthesis 200 forces inner wall 126 outward, away from centerline $CL_d$ of descending aorta 110 such that inner wall 126 approaches normal aortic wall position 134, natural lumen 132 through descending aorta 110 is generally restored, and the position of prosthesis 200 is maintained with respect to tear 124 of aortic dissection 102. More specifically, when prosthesis 200 is deployed at the site of aortic dissection 102 and in the radially expanded deployed configuration, graft material 204 seals tear 124 such that blood no longer flows into false lumen 130, as shown in FIG. 2.

While tear 124 is sealed by graft material 204 of prosthesis 200 and natural lumen 132 of descending aorta 110 is restored, graft material 204 would block blood flow to any arteries emanating from the portion of the vessel bypassed by prosthesis 200. Accordingly, conventional prostheses are not placed in the descending aorta such that they would block branch arteries such as the celiac artery, the superior mesenteric artery, or the renal arteries, or accommodations must be made to maintain blood flow to these branch arteries. Further, even when located above the celiac artery, prosthesis 200 may block blood flow to some smaller arteries that provide blood flow to the spine, such as intercostal arteries 120 and subcostal arteries 122. Although not desirable, this is sometimes accepted in conventional prostheses. Further, a conventional prosthesis 200 is generally not used for a dissection in the ascending aorta 106 and aortic arch 108, as blocking blood flow to the great vessels of the aortic arch is unacceptable.

Further, the outward radial force of seal stents (at proximal and distal ends of stent-graft prosthesis 200) of conventional graft prostheses tends to create new dissections.

Accordingly, there is a need for an improved, dissection specific stent-graft prosthesis system and method to repair an aortic dissection that reduces the possibility of creating new dissections, does not restrict blood flow to branch arteries of the aorta, may be utilized within the ascending aorta and aortic arch, and has excellent flexibility for easy delivery to the treatment site.

SUMMARY OF THE INVENTION

Embodiments hereof relate to a dissection prosthesis system for implantation within a blood vessel. The dissection prosthesis system includes a first prosthesis and a second prosthesis. The first prosthesis includes a generally tubular shape, a radially compressed delivery configuration and a radially expanded deployed configuration, a first stent ring, a second stent ring, a first graft material band connecting the first stent ring to the second stent ring, a third stent ring, and a second graft material band connecting the second stent ring to the third stent ring. The first graft material band is disposed between the first stent ring and the second stent ring and the second graft material band is disposed between the second stent ring and the third stent ring. The second stent ring includes a plurality of openings to enable fluid flow from a lumen of the first prosthesis through the plurality of openings. The first and second graft material bands may also include a plurality of band openings to enable fluid flow from the lumen of the first prosthesis through the plurality of band openings. The second prosthesis includes a generally tubular shape, and a radially compressed delivery configuration and a radially expanded deployed configuration. The second prosthesis includes a stent and a graft material coupled to the stent. The second prosthesis is configured to be disposed within the lumen of the first prosthesis.

Embodiments hereof also relate to a prosthesis having a generally tubular shape, a proximal end and a distal end, and a radially collapsed delivery configuration and a radially expanded deployed configuration. The prosthesis includes a plurality of stent rings, and a plurality of graft material bands. Each of the plurality of stent rings includes a plurality of proximal apices, a plurality of distal apices, and a plurality of strut portions. Each strut portion is disposed between and couples to one of the plurality of proximal apices and one of the plurality of distal apices. Each of the plurality of stent rings includes a plurality of openings between the respective strut portions, proximal apices, and distal apices. Each graft material band includes a proximal edge portion and a distal edge portion. Each one of the plurality of graft material bands is disposed between and couples together a respective adjacent pair of the plurality of stent rings. A first stent ring of the adjacent pair is coupled to a second stent ring of the adjacent pair only by one of the plurality of graft material bands. The plurality of openings enables fluid flow from a lumen of the prosthesis through the openings. The plurality of graft material bands may also include band openings therethrough to enable fluid flow from the lumen of the prosthesis through the band openings of the graft material bands.

Embodiments hereof also relate to a method for treating a dissection. A first prosthesis is delivered to the site of the dissection and deployed from a radially compressed delivery configuration to a radially expanded deployed configuration. The first prosthesis includes a plurality of stent rings, a plurality of graft material bands, and a plurality of openings through each of the plurality of stent rings. The plurality of graft material bands are disposed in an alternating configuration with the plurality of stent rings. The plurality of openings enables blood flow from a lumen of the first prosthesis through the plurality of openings. The plurality of graft material bands may also include a plurality of band openings therethrough to enable blood flow from the lumen of the first prosthesis through the plurality of band openings. A second prosthesis in a radially compressed delivery configuration is delivered to the site of the dissection and within the first prosthesis. The second prosthesis is deployed from the radially compressed delivery configuration to a radially expanded deployed configuration. The second prosthesis exerts a radially outward force from within the first prosthesis.

DETAILED DESCRIPTION

Specific embodiments of the present invention are now described with reference to the figures, wherein like reference numbers indicate identical or functionally similar elements. The terms "distal" and "proximal", when used in the following description to refer to a catheter or delivery system, are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal", when used in the following description to refer to a device or system to be implanted into a native artery, such as a prosthesis or dissection prosthesis, are used with reference to the direction of blood flow from the heart. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Furthermore, there is no intention to be bound by any expressed or implied theory presented in the preceding technical field, background, brief summary, or the following detailed description.

Figure 1:
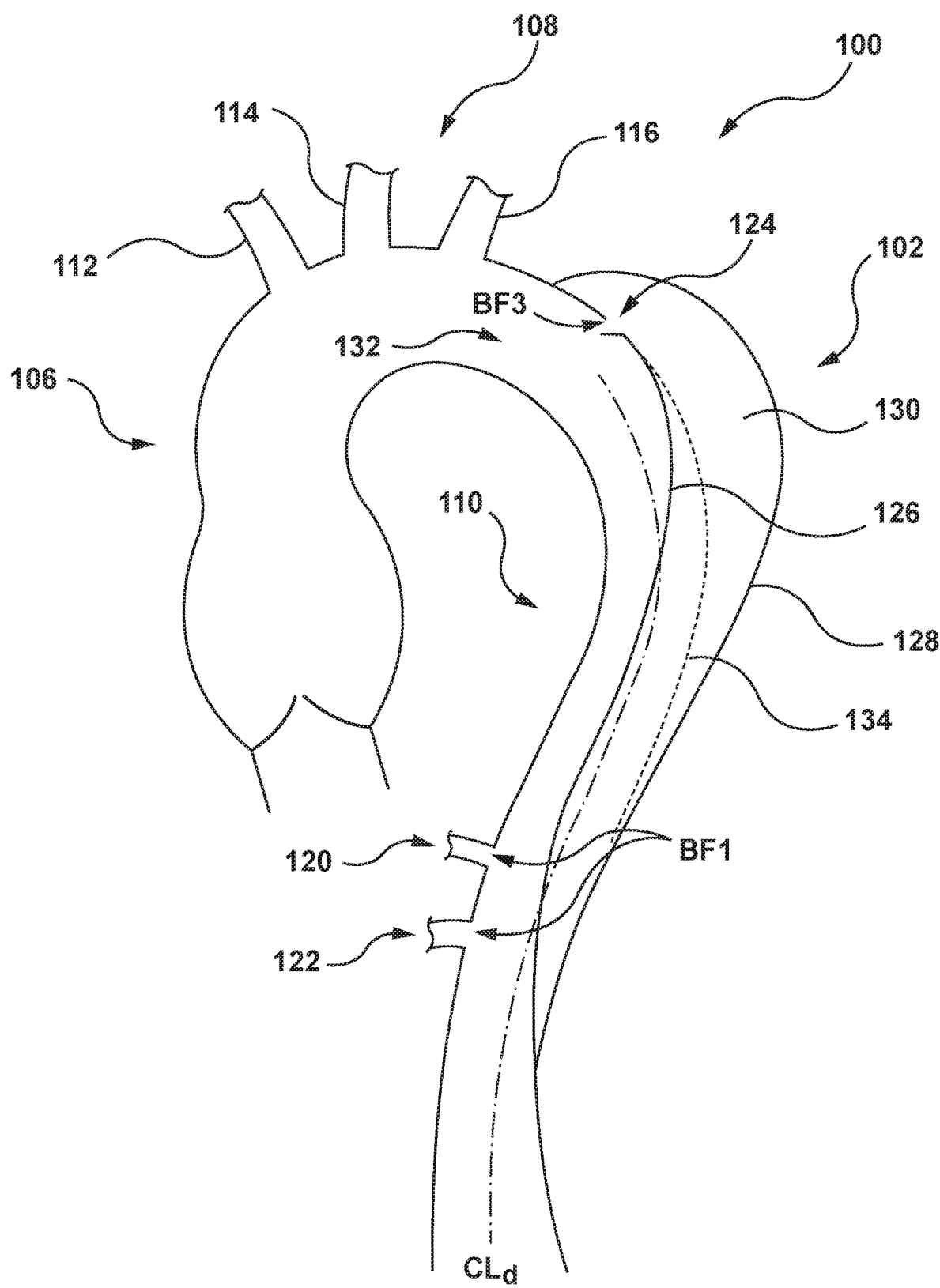
FIG. 1 is a cutaway side illustration of a dissected aorta.
Figure 2:
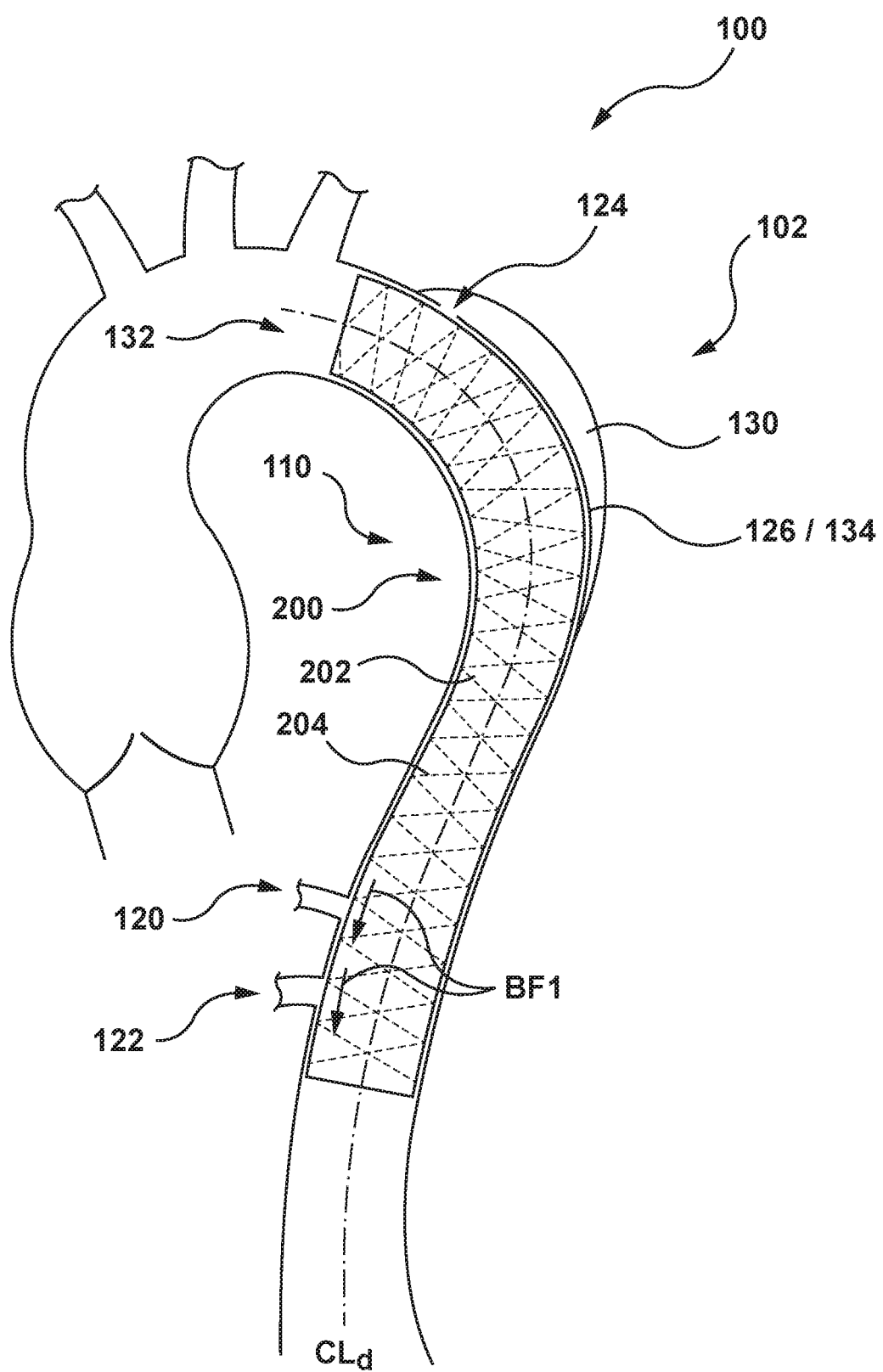
FIG. 2 is a cutaway side illustration of a prior art treatment of the dissected aorta of FIG. 1.
Figure 3:
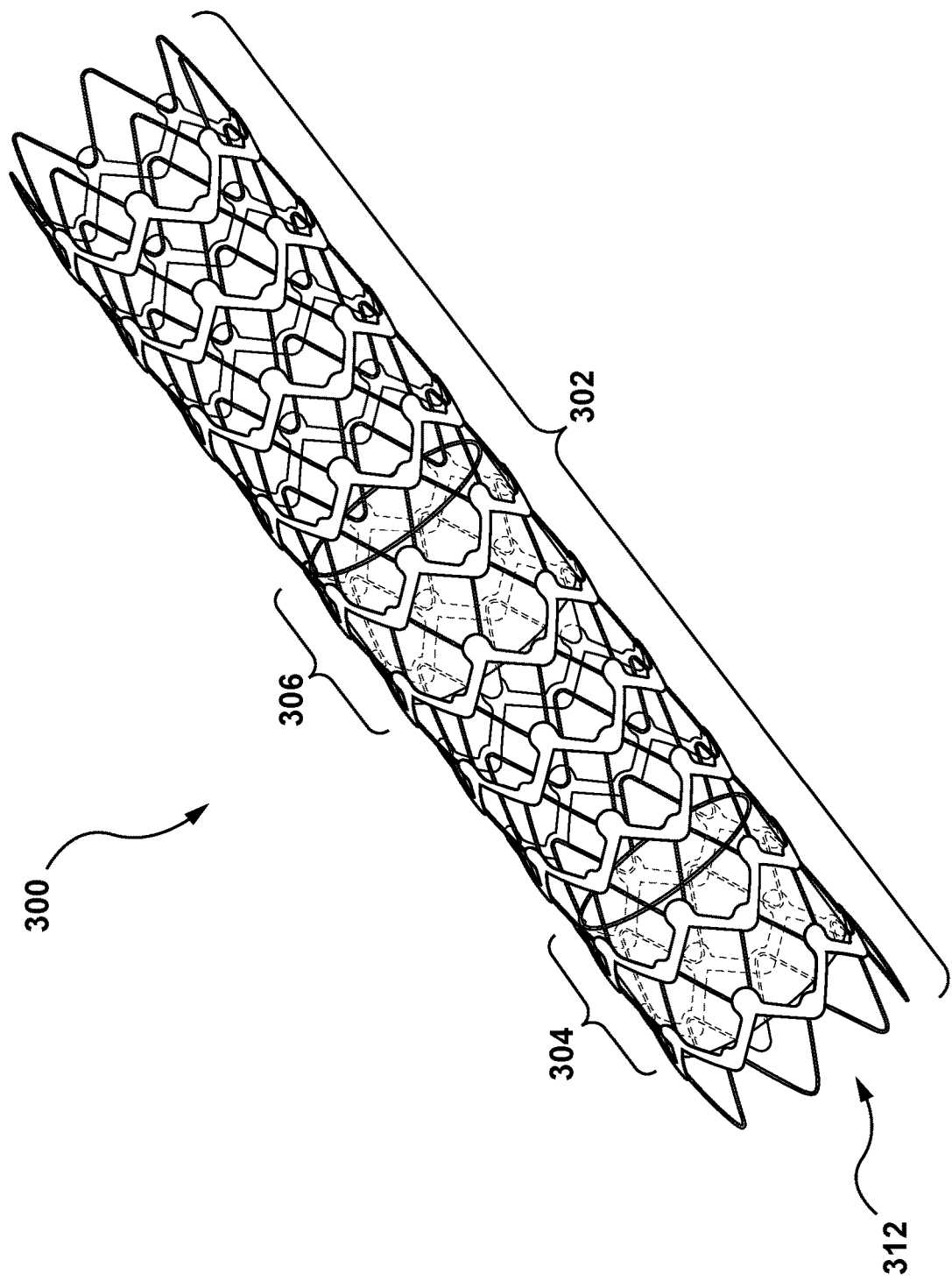
FIG. 3 is a perspective illustration of an embodiment of a dissection prosthesis system in a radially expanded deployed configuration.
Figure 4:
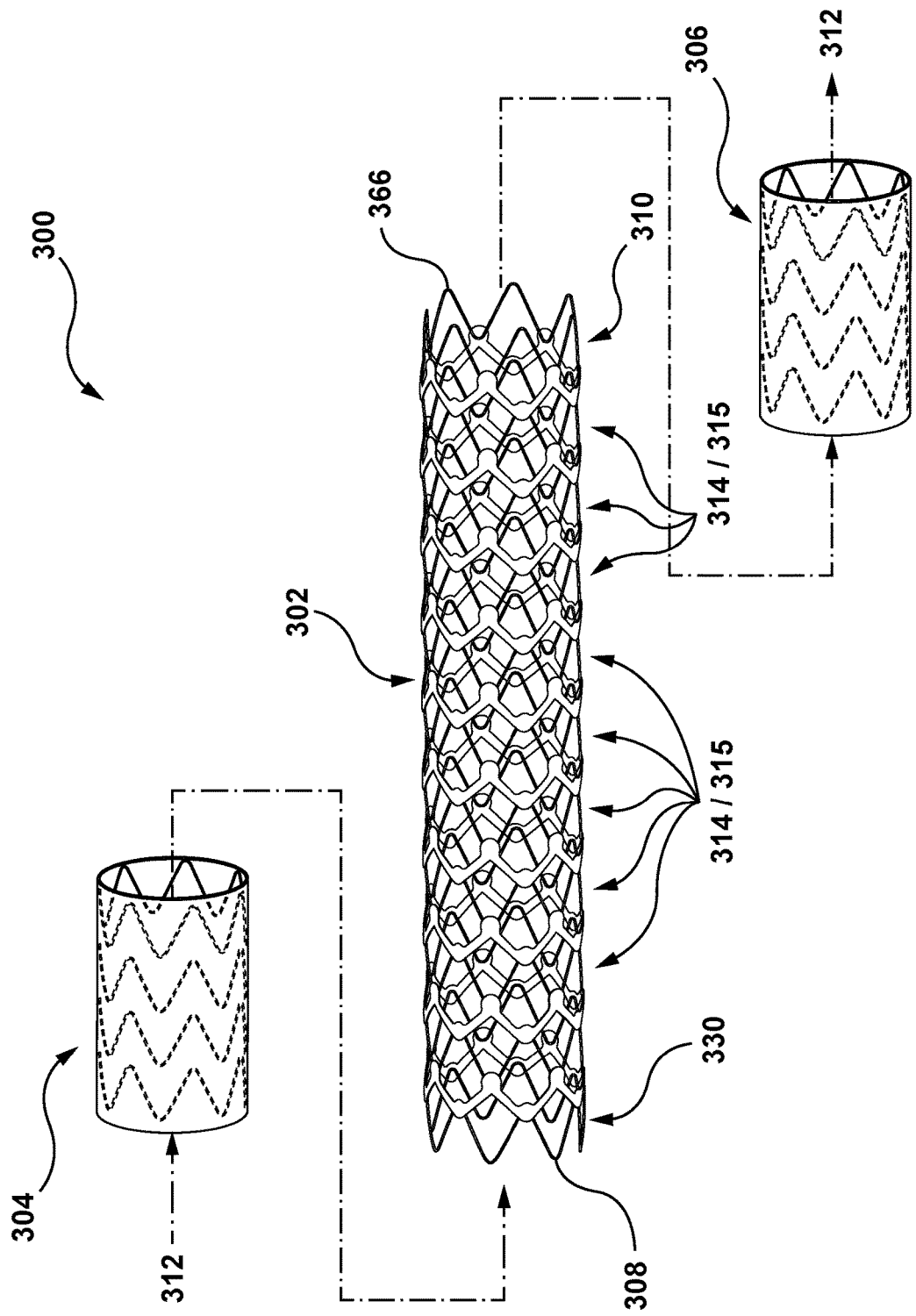
FIG. 4 is an exploded perspective view of the dissection prosthesis system of FIG. 3, wherein a first prosthesis, a second prosthesis, and a third prosthesis are in a radially expanded deployed configuration.

With the above understanding in mind, a dissection prosthesis system 300 according to an embodiment of the present disclosure is shown in FIG. 3 and in greater detail in FIGS. 4-13. In an embodiment, dissection prosthesis 300 includes a first prosthesis 302, a second prosthesis 304, and a third prosthesis 306 for treatment of an aortic dissection, as shown in FIGS. 3-4 and described in greater detail below. Various features of the components of dissection prosthesis system 300 reflected in FIGS. 3-13 and described below can be modified or replaced with differing structures and/or mechanisms. Dissection prosthesis system 300, described in greater detail below, is merely an exemplary embodiment of a dissection prosthesis system according to an embodiment hereof and modifications can be made to the embodiments described herein without departing from the spirit and scope of the present invention. The present disclosure is in no way limited to first prosthesis 302, second prosthesis 304, and third prosthesis 306, shown and described below. Components of dissection prosthesis system 300 may assume different forms and construction based upon application. Therefore, the following detailed description is not meant to be limiting.

Figure 5:
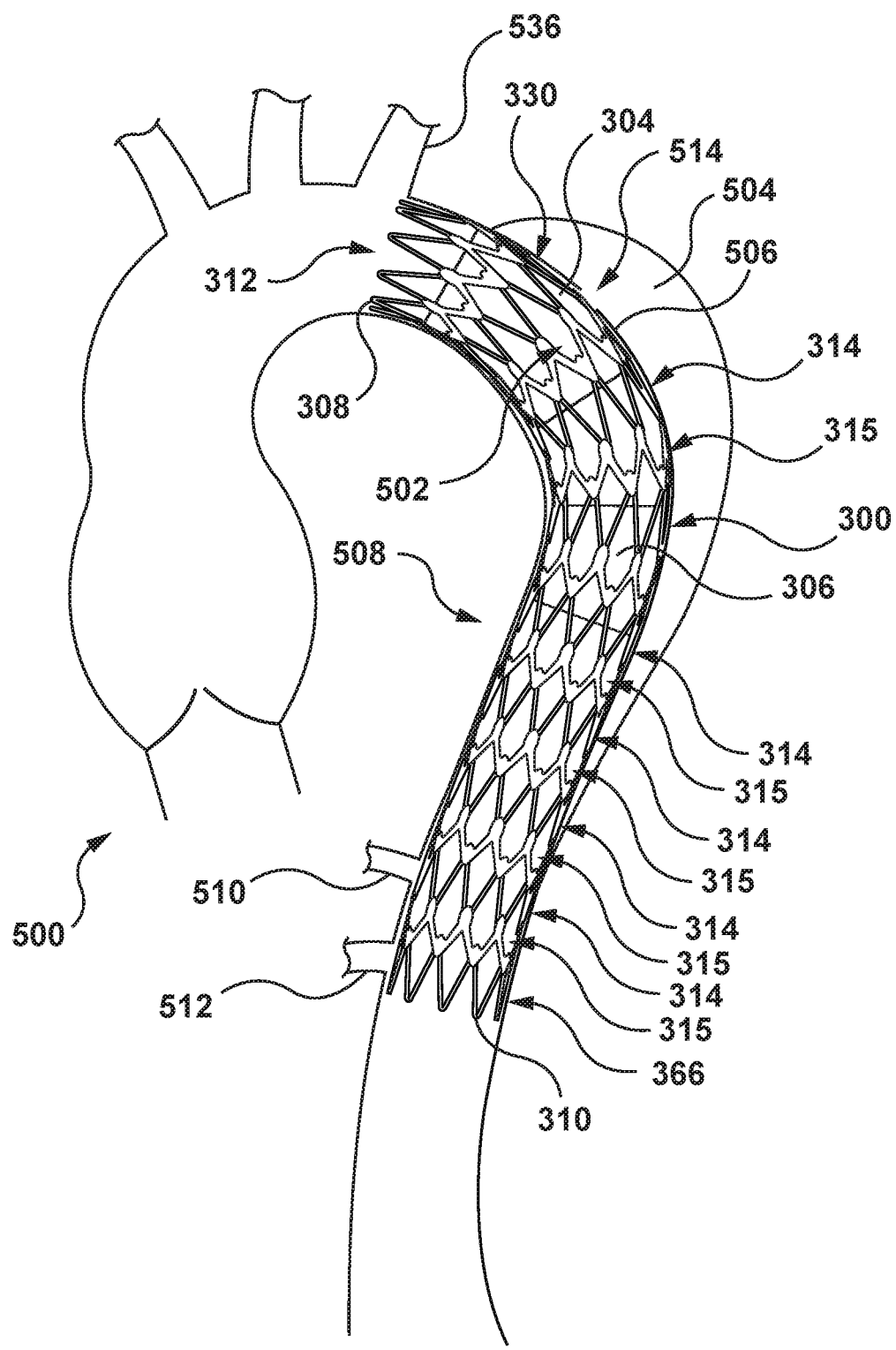
FIG. 5 is a cutaway side illustration of the dissection prosthesis system of FIG. 3 deployed within a descending aorta.

Dissection prosthesis system 300 is of a generally tubular configuration and includes first prosthesis 302, second prosthesis 304, third prosthesis 306, a proximal end 308, and a distal end 310 defining a lumen 312, therein, as shown in FIGS. 3-4 and described in greater detail below. The term "generally tubular", as used herein, is not meant to be restrictive. Thus, a "generally tubular" device is not restricted to a cylinder. Instead, it may include other shapes, such as, but not limited to, a tapered tube, and oblong tube, and other shapes suitable for use in a lumen. Dissection prosthesis system 300 is configured to be disposed within an aorta 500 at the site of an aortic dissection 502, as shown in FIG. 5. Dissection prosthesis system 300 includes a radially compressed delivery configuration (FIG. 16) and a radially expanded deployed configuration, as shown in FIGS. 3-13. Dissection prosthesis system 300 is further configured such that dissection prosthesis 300 seals a tear 514 of aortic dissection 502 and isolates a false lumen 504. Dissection prosthesis system 300 also enables blood flow from lumen 312 through a plurality of openings 314 and 315 to branch and ancillary arteries such as, but not limited to intercostal arteries 510 and subcostal arteries 512. Dissection prosthesis system 300 is also configured to maintain the position of dissection prosthesis system 300 at the site of aortic dissection 502. Dissection prosthesis system is also configured to minimize the potential of dissection prosthesis system 300 penetrating an inner wall 506 of a descending aorta 508, as described in greater detail below. Further, the dissection prosthesis system 300 enables access to branch vessels by catheters or other such devices through the openings 314 in stent rings and/or band openings 315 in a plurality of graft material bands (described in more detail below).

Figure 6:
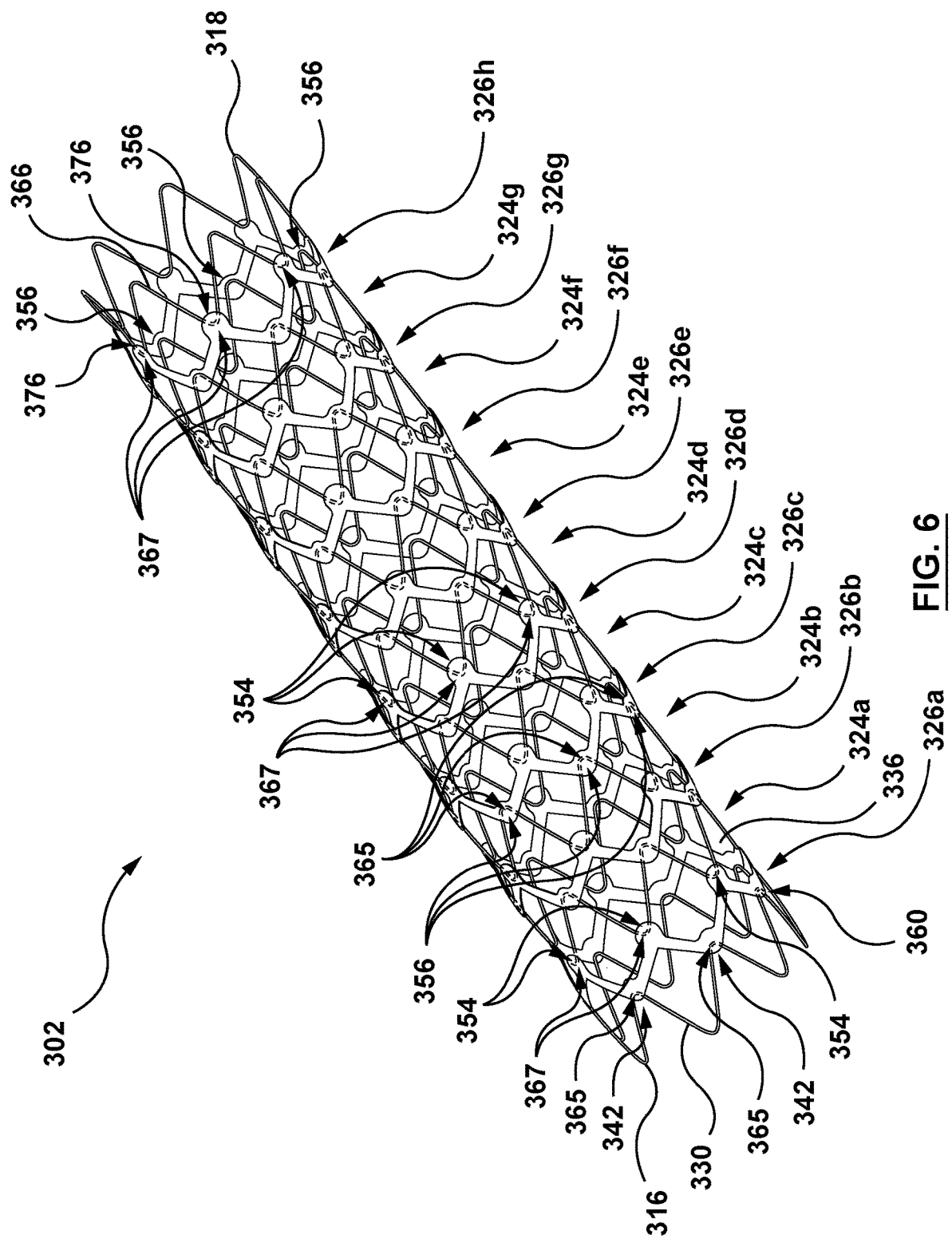
FIG. 6 is a close up perspective illustration of an embodiment of a first prosthesis of the dissection prosthesis system of FIG. 3 in the radially expanded deployed configuration.

FIG. 6 illustrates an embodiment of first prosthesis 302 of dissection prosthesis system 300. First prosthesis 302 is of a generally tubular configuration and includes a proximal end 316 and a distal end 318, and defines a lumen 320 therein. First prosthesis 302 includes a proximal stent ring 330, a first stent ring 324a, a second stent ring 324b, a third stent ring 324c, a fourth stent ring 324d, a fifth stent ring 324e, a sixth stent ring 324f, a seventh stent ring 324g, a first graft material band 326a, a second graft material band 326b, a third graft material band 326c, a fourth graft material band 326d, a fifth graft material band 326e, a sixth graft material band 326f, a seventh graft material band 326g, an eighth graft material band 326h, and a distal stent ring 366. First prosthesis 302 includes a radially compressed delivery configuration (FIG. 16) and a radially expanded deployed configuration. First prosthesis 302 is configured to be disposed within aorta 500 such that, in an embodiment, proximal end 308 is disposed distal of left subclavian artery 536 and proximal of tear 514 of aortic dissection 502, and distal end 310 is disposed distal of tear 514 of aortic dissection 502 when in the radially expanded deployed configuration at the treatment site, as shown in FIG. 5. First prosthesis 302 is further configured such that an outward radial force of first prosthesis 302 in the radially expanded deployed configuration forces an outer surface of first prosthesis 302 to engage an aortic inner wall v, maintaining first prosthesis 302 at the treatment site. First prosthesis 302 may be self-expanding or balloon expandable, preferably self-expanding.

Figure 7:
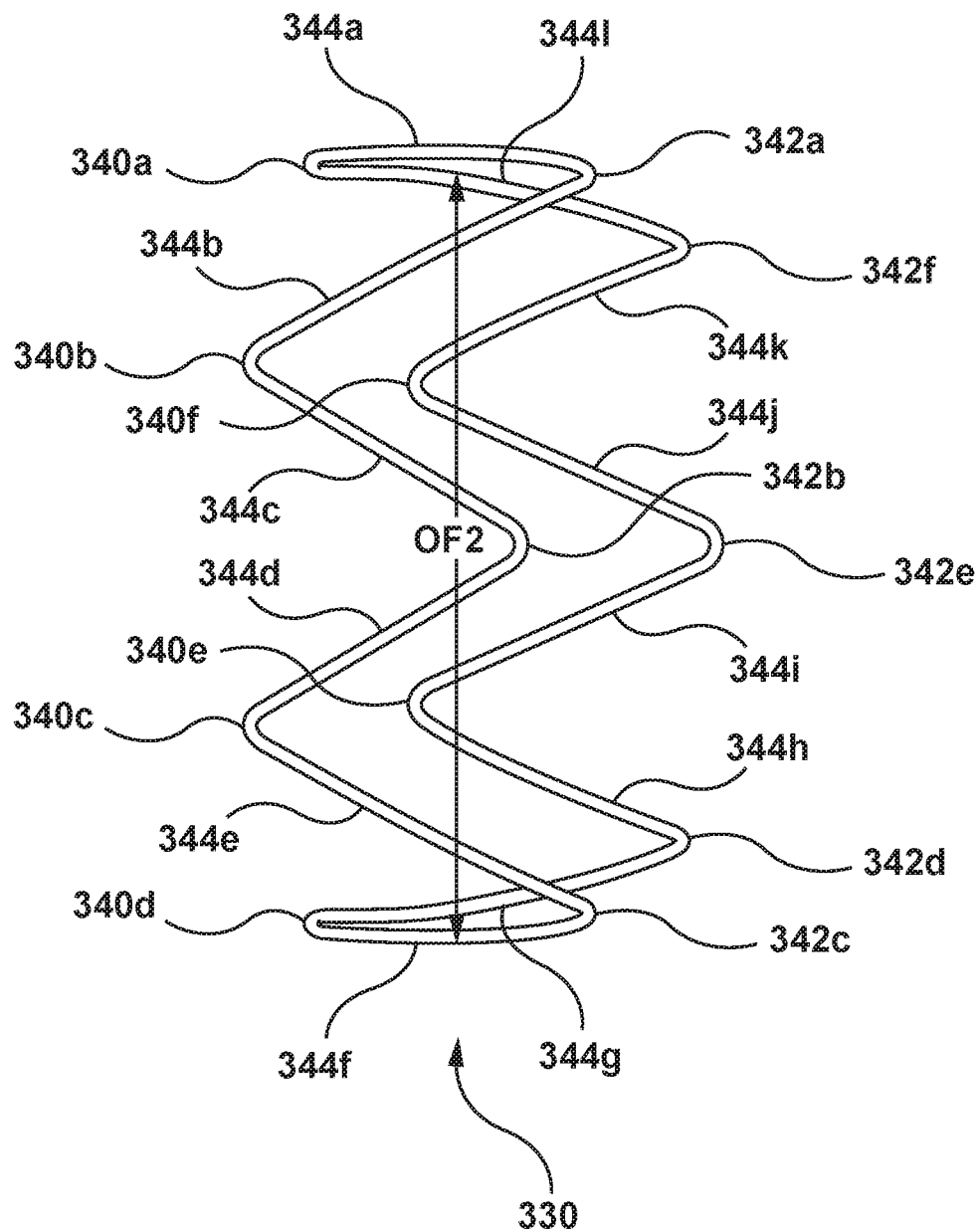
FIG. 7 is a close up perspective illustration of a proximal stent ring of the first prosthesis of FIG. 6 in the radially expanded deployed configuration.
Figure 8:
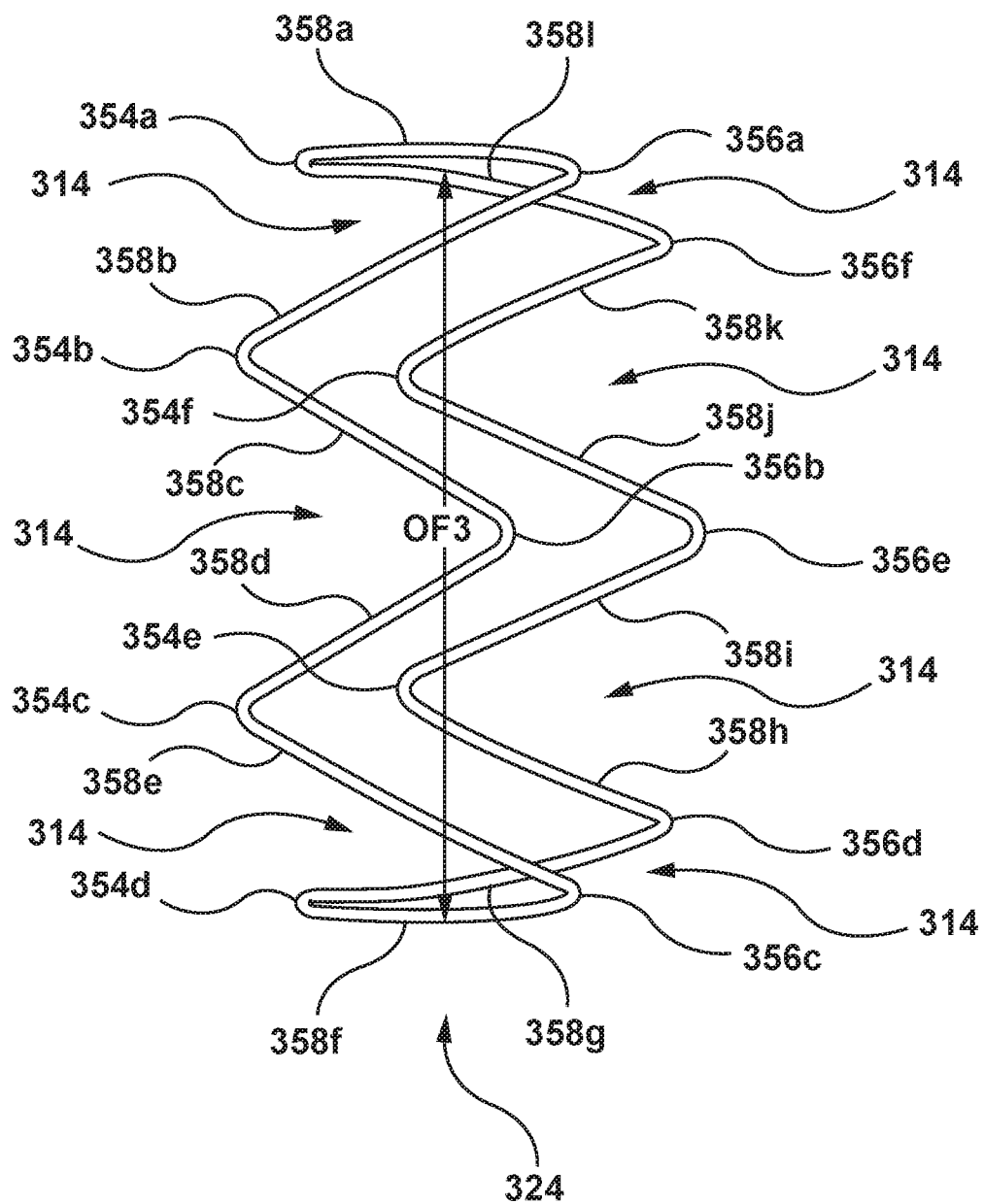
FIG. 8 is a close up perspective illustration of an embodiment of a stent ring of the first prosthesis of FIG. 6 in the radially expanded deployed configuration.

FIG. 7 shows an embodiment of proximal stent ring 330 of first prosthesis 302. Proximal stent ring 330 is of a generally ring-like configuration and is formed of a continuous wound structure that includes a plurality of proximal apices 340a/340b/340c/340d/340e/340f, generally known as proximal apices 340, a plurality of distal apices 342a/342b/342c/342d/342e/342f, generally known as distal apices 342 and a plurality of strut portions 344a/344b/344c/344d/344e/344f/344g/344h/344i/344j/344k/344l, generally known as strut portions 344, as shown in FIG. 8. Strut portions 344 are configured such that each strut portion 344 is disposed between and couples an adjacent proximal apex 340 to an adjacent distal apex 342. Proximal stent ring 330 is radially expandable from a radially compressed delivery configuration (FIG. 16) to a radially expanded deployed configuration, as shown in FIGS. 3-7 and 17-21. In an embodiment, when proximal stent ring 330 is in the radially expanded deployed configuration, it exerts a second outward radial force OF2 against walls of the aorta. In an embodiment, second outward radial force OF2 may be in the range of 400-670 pascal (PA). In an embodiment second outward radial force OF2 is less than outward radial force OF1 of proximal and distal stents of conventional stent-grafts. In an embodiment second outward radial force OF2 is less than a third outward radial force OF3 of each of stent rings 324 as described below. Stent ring 330 is further configured to provide a flexible, conformable stent, which expands uniformly. Stent ring 330 may be formed, for example, and not by way of limitation, of a nickel titanium alloy, Nitinol, a nickel-cobalt-chromium-molybdenum alloy (MP35N), stainless steel, high spring temper steel, or any other metal or composite having elastic properties to permit extension and recoil suitable for purposes of the present disclosure.

While first prosthesis 302 is shown with one proximal stent ring 330 in FIGS. 4-6, it is not meant to limit the design, and other configurations with additional proximal stent rings 330 may be utilized. Additionally, while proximal stent ring 330 is shown with six (6) proximal apices 340, six (6) distal apices 342, and twelve (12) strut portions 344 it is not meant to limit the design, and other configurations with more or fewer proximal apices, distal apices, and strut portions may be utilized.

First stent ring 324a, second stent ring 324b, third stent ring 324c, fourth stent ring 324d, fifth stent ring 324e, sixth stent ring 324f, and seventh stent ring 324g are generally known as stent rings 324 and are of a generally ring-like configuration. In an embodiment shown in FIG. 8, each stent ring 324 includes a plurality of proximal apices 354a/354b/354c/354d/354e/354f, generally known as proximal apices 354, a plurality of distal apices 356a/356b/356c/356d/356e/356f, generally known as distal apices 356, and a plurality of strut portions 358a/358b/358c/358d/358e/358f/358g/358h/358i/358j/340k/358l, generally known as strut portions 358, and a plurality of openings 314. Strut portions 358 are configured such that each strut portion 358 is disposed between and couples an adjacent proximal apex 354 to an adjacent distal apex 356. The plurality of openings 314 are defined between respective strut portions 358, proximal apices 354, and distal apices 356, as shown in FIG. 8. Each stent ring 324 is disposed between proximal stent ring 330 and distal stent ring 366 as shown in FIG. 6 and as described below. Stent rings 324 are radially expandable from a radially compressed delivery configuration (FIG. 16) to a radially expanded deployed configuration (FIGS. 3-6, 8, and 17-21). Each stent ring 324 is configured such that each stent ring 324 in the radially expanded deployed configuration exerts a third outward radial force OF3. In an embodiment, third outward radial force OF3 may be in the range of 800-1340 pascal (PA). In an embodiment third outward radial force OF3 is greater than second outward radial force OF2 of proximal stent ring 330 and greater than fourth outward radial force OF4 of distal stent ring 366, described below. In an embodiment, third radial outward force OF3 is approximately 1.5 to 3 times second outward radial force OF2 and approximately 1.5 to 3 times fourth outward radial force OF4. In an embodiment third outward radial force OF3 is approximately twice second radial outward force OF2 and approximately twice fourth radial outward force OF4. Openings 314 of stent rings 324 are configured to enable blood flow from lumen 320 of first prosthesis 302 through openings 314 to ancillary or branch arteries emanating from the aorta, such as ancillary arteries 510, 512 shown in FIG. 5. Stent rings 324 may be formed, for example, and not by way of limitation, of a nickel-titanium alloy, Nitinol, a nickel-cobalt-chromium-molybdenum alloy (MP35N), stainless steel, high spring temper steel, or any other metal or composites having properties suitable for purposes of the present disclosure.

While each stent ring 324 is shown in FIG. 8 with six (6) proximal apices 354, six (6) distal apices 356, and twelve (12) strut portions 358, it is not meant to limit the design, and other configurations with more or fewer proximal apices, distal apices, and strut portions may be utilized. Further, other types of stent rings with openings may be used.

Figure 9:
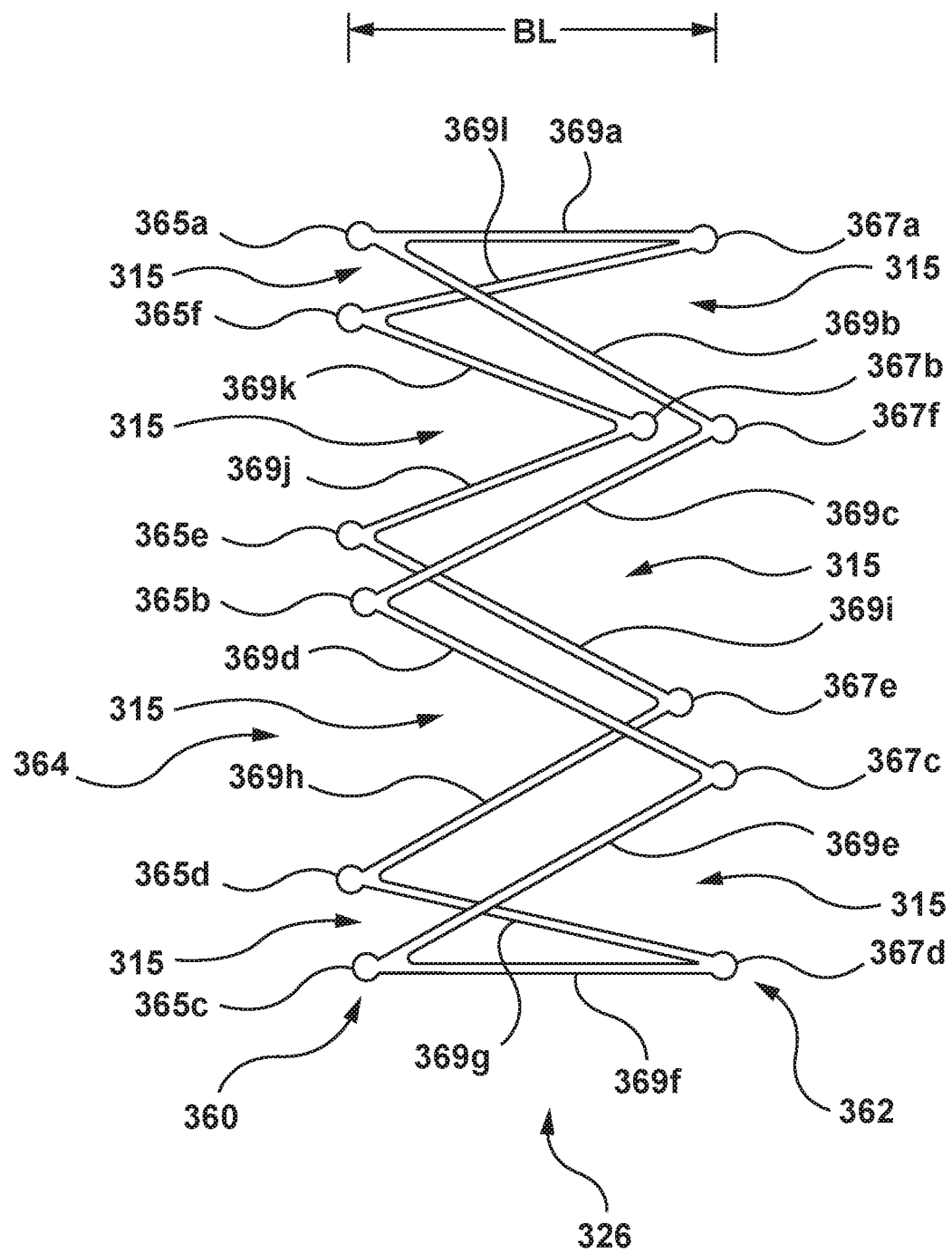
FIG. 9 is a close up perspective illustration of an embodiment of a graft material band of the first prosthesis of FIG. 6.

First graft material band 326a, second graft material band 326b, third graft material band 326c, fourth graft material band 326d, fifth graft material band 326e, sixth graft material band 326f, seventh graft material band 326g, and eighth graft material band 326h are generally known as graft material bands 326. In an embodiment shown in FIG. 9, each graft material band 326 is of a generally tubular, zig-zag configuration and includes a proximal end 360 and a distal end 362 defining a lumen 364 therein. In an embodiment shown in FIG. 9 each graft material band 326 further includes a plurality of proximal landing points 365a/365b/365c/365d/365e/365f, generally known as proximal landing points 365, a plurality of distal landing points 367a/367b/367c/367d/367e/367f, generally known as distal landing points 367, a plurality of connector portions 369a/369b/369c/369d/369e/369f/369g/369h/369i/369j/369k/369l, generally known as connector portions 369, and a plurality of band openings 315. Connector portions 369 are configured such that each connector portion 369 is disposed between and couples an adjacent proximal landing point 365 to an adjacent distal landing point 367. The plurality of band openings 315 are defined between respective connector portions 369, proximal landing points 365, and distal landing points 367, as shown in FIG. 9. Graft material bands 326 are configured such that each graft material band 326 couples together adjacent stent rings 324. Graft material bands 326 are further configured such that graft material band 326a couples proximal stent ring 330 with adjacent stent ring 324a, and graft material band 326h couples distal stent ring 366 with adjacent stent ring 324g. Each graft material band 326 is disposed between adjacent stent rings 324, or between a stent ring 324 and adjacent proximal stent ring 330, or between a stent ring 324 and adjacent distal stent ring 366, as shown in FIG. 6. Graft material band 326 has a longitudinal length BL, which may vary based upon the application need. Each graft material band 326 may be formed, for example, and not by way of limitation, of woven polyester such as polyethylene terephthalate, polytetrafluoroethylene (PTFE), stretched polyester (BoPET, such as Mylar), or any other material suitable for purposes of the present disclosure.

While each graft material band 326 is shown in FIG. 9 with six (6) proximal landing points 365, six (6) distal landing points, 367, and twelve (12) connector portions 369, it is not meant to limit the design, and other configurations with more or fewer proximal landing points, distal landing points, and connector portions may be utilized.

While each graft material band 326 is shown in FIG. 9 with proximal landing point 365 and each distal landing point 367 as including a generally flattened disk shape, and each connector portion 369 as having a generally flat, rectangular shape, it is not meant to limit the design, and other shapes and configurations of proximal landing points distal landing points, and connector portions maybe utilized. Further, other types of graft material bands with various shapes may be used. Further, each graft material band need not be identical to other graft material bands.

Figure 10:
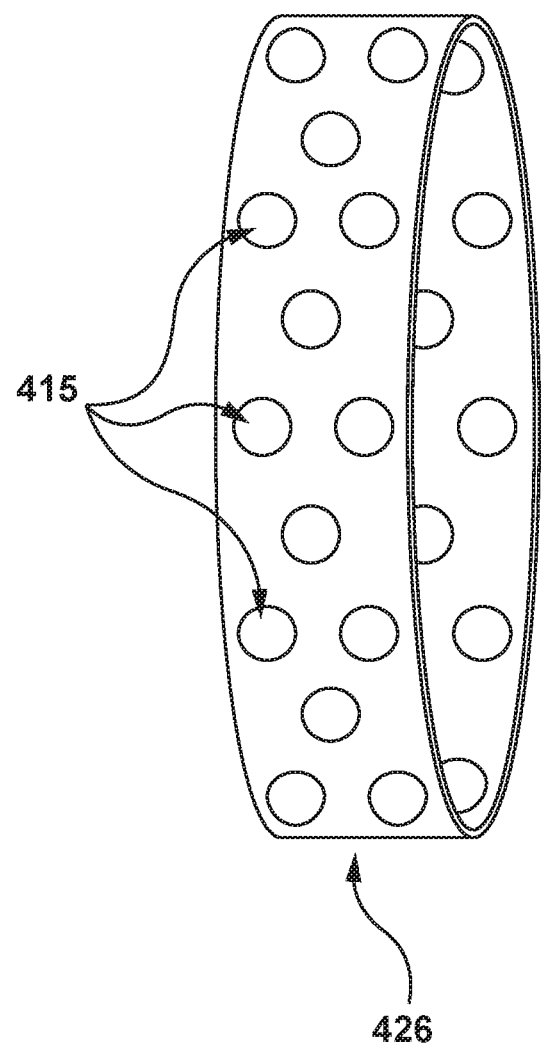
FIG. 10 is a close up perspective illustration of another embodiment of a graft material band of the first prosthesis of FIG. 6.

While each graft material band 326 is described herein with a zig-zag configuration, this is not meant to limit the design and other configurations may be utilized, including, but not limited to a generally tubular band 426 with openings 415, as shown in FIG. 10.

Figure 11:
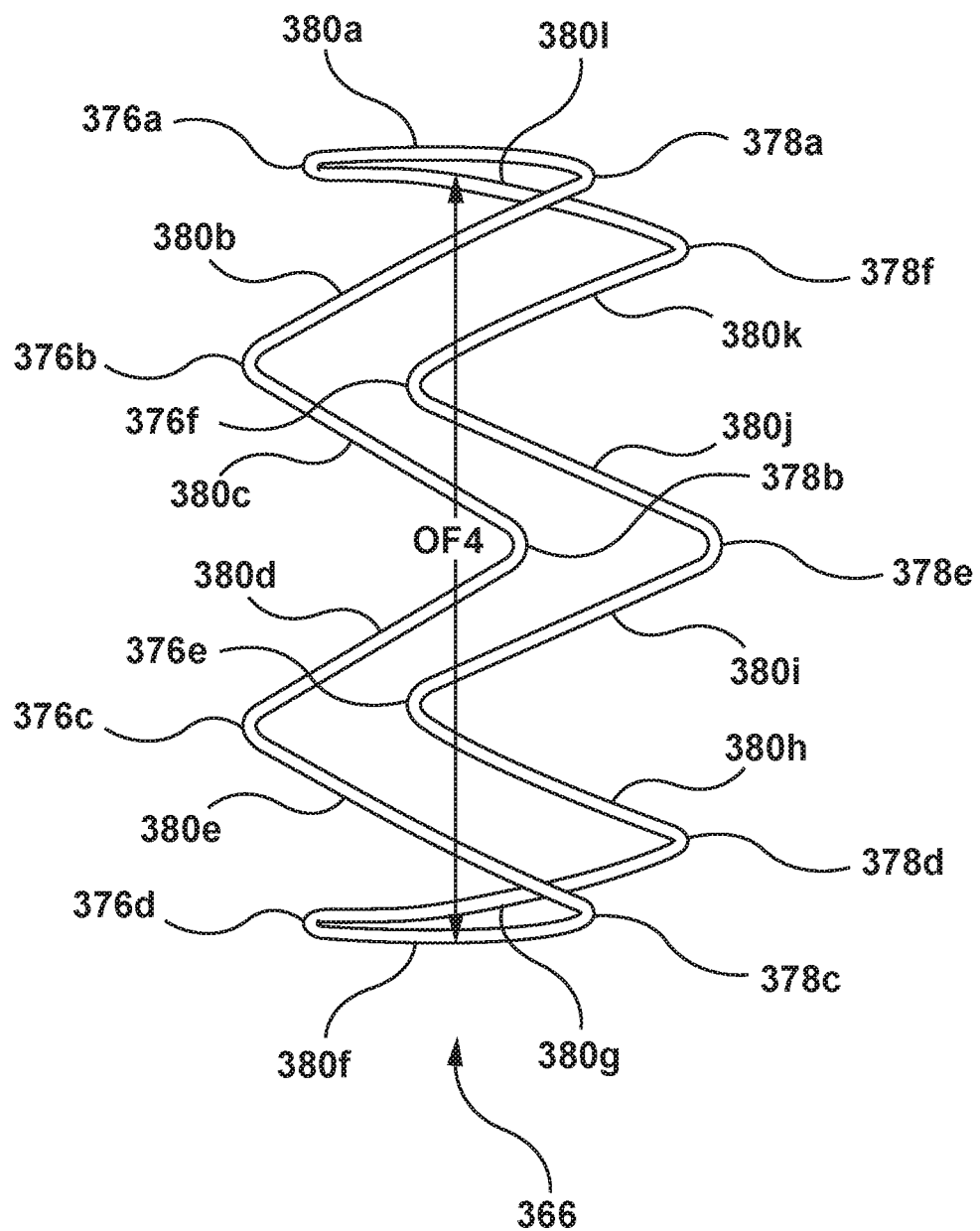
FIG. 11 is a close up perspective illustration of an embodiment of a distal stent ring of the first prosthesis of FIG. 6 in the radially expanded deployed configuration.

FIG. 11 shows an embodiment of distal stent ring 366 of first prosthesis 302. Distal stent ring 366 is of a generally ring-like configuration and is formed of a continuous wound structure that includes a plurality of proximal apices 376a/376b/376c/376d/376e/376f, generally known as proximal apices 376, a plurality of distal apices 378a/378b/378c/378d/378e/378f, generally known as distal apices 378 and a plurality of strut portions 380a/380b/380c/380d/380e/380f/380g/380h/380i/380j/380k/380l, generally known as strut portions 380, as shown in FIG. 11. Strut portions 380 are configured such that each strut portion 380 is disposed between and couples an adjacent proximal apex 376 to an adjacent distal apex 378. Distal stent ring 366 is radially expandable from a radially compressed delivery configuration (FIG. 16) to a radially expanded deployed configuration, as shown in FIGS. 3-6, 12, and 17-21. In an embodiment, when distal stent ring 366 is in the radially expanded deployed configuration, it exerts a fourth outward radial force OF4 against walls of the aorta. In an embodiment, fourth outward radial force OF4 may be in the range of 400-670 pascal (PA). In an embodiment fourth outward radial force OF4 is less than outward radial force OF1 of proximal and distal stents of conventional stent-grafts. In an embodiment, fourth outward radial force OF4 of distal stent ring 366 is less than third outward radial force OF3 of each stent ring 324. Distal stent ring 366 is further configured to provide a flexible, conformable stent, which expands uniformly and provides fourth outward radial force OF4 as described previously. Stent ring 366 may be formed, for example, and not by way of limitation, of a nickel-titanium alloy, Nitinol, a nickel-cobalt-chromium-molybdenum alloy (MP35N), stainless steel, high spring temper steel, or any other metal or composite having elastic properties to permit extension and recoil suitable for purposes of the present disclosure.

While first prosthesis 302 is shown with one distal stent ring 366 in FIGS. 3-6, 14-15, and 17-21, it is not meant to limit the design, and other configurations with additional distal stent rings 366 may be utilized. Additionally, while distal stent ring 366 is shown in FIG. 11 with six (6) proximal apices 376, six (6) distal apices 378, and twelve (12) strut portions 380 it is not meant to limit the design, and other configurations with more or fewer proximal apices, distal apices, and strut portions may be utilized.

Referring back to FIG. 6, first prosthesis 302 is configured such that a graft material band 326 is disposed between and couples together adjacent stent rings 324. First prosthesis 302 is further configured such that a graft material band 326a is disposed between and couples together proximal stent ring 330 and adjacent stent ring 324a, and a graft material band 326h couples together distal stent ring 366 and adjacent stent ring 324g.

More specifically, in an embodiment, proximal edge 360 of first graft material band 326a is disposed about an outer surface of distal apices 342 of proximal stent ring 330 and distal apices 342 are coupled to proximal landing points 365, as shown in FIG. 6. Further, distal edge 362 of first graft material band 326a is disposed about an outer surface of proximal apices 354 of first stent ring 324a and proximal apices 354 are coupled to distal landing points 367. Stated another way, proximal stent ring 330 is coupled to adjacent first stent ring 324a only by first graft material band 326a disposed therebetween. Distal apices 342 of proximal stent ring 330 are coupled to proximal landing points 365 of first graft material band 326a and proximal apices 354 of first stent ring 324a are coupled to distal landing points 367 of first graft material band 326a in a manner such as, but not limited to sutures, adhesives, or other methods suitable for the purposes disclosed herein.

Second stent ring 324b, third stent ring 324c, fourth stent ring 324d, and fifth stent ring 324e, and distal stent ring 366 are coupled to each adjacent stent ring by a graft material band 326, as shown in FIG. 6. Stated another way, proximal stent ring 330, each stent ring 324, and distal stent ring 366 is coupled to an adjacent stent ring 324 only by a graft material band 326 disposed therebetween.

In an embodiment, the apices of the stent rings are coupled to respective graft material bands using two (2) sutures at each connection location (i.e., each apex). In another embodiment, the apices of the stent rings are coupled to the respective graft material bands using one (1) suture to five (5) sutures at each connection location (i.e., each apex). Other connections between the stent rings and the respective graft material bands may also be used, such as, but not limited to, adhesives, fusion, and other mechanical or chemical connections.

In an embodiment, the apices of stent rings are coupled to respective graft material bands such that an inner surface of the landing points of the graft material bands covers an outer surface of the apices of the stent rings. In such an embodiment, the graft material bands protect the vessel wall against potential damage by the apices of the stent rings. However, in other embodiments, an outer surface of the graft material bands may be coupled to an inner surface of the apices of the stent rings, or some apices may be disposed inside the panging points and some apices may be disposed outside the landing points.

Openings 314 and 315 of first prosthesis 302 are configured to enable fluid flow from lumen 320 of first prosthesis 302 through openings 314 and 315. Stated another way, openings 314 and 315 are configured to enable blood flow from aorta 500 through openings 314, 315 to branch and ancillary arteries such as, but not limited to intercostal arteries 510 and subcostal arteries 512, as shown in FIG. 5.

While first prosthesis 302 is shown in with seven (7) stent rings and eight (8) graft material bands, this is not meant to limited design, and more or fewer stent rings 324 and adjacent graft material bands 326 may be utilized.

While first prosthesis 302 is shown in FIG. 5 as enabling fluid flow from lumen 320 to branch and ancillary arteries of the descending aorta, this is not meant to limit the design, and first prosthesis 302 may enable fluid flow to any artery of the aorta, as described in greater detail below.

While branch and ancillary arteries such as intercostal artery 510 and subcostal artery 512 are shown in FIG. 5 as two (2) vessels, this is for illustrative purposes only and intercostal arteries 510 and subcostal arteries 512 may each represent a plurality of branch and ancillary arteries.

Figure 12:
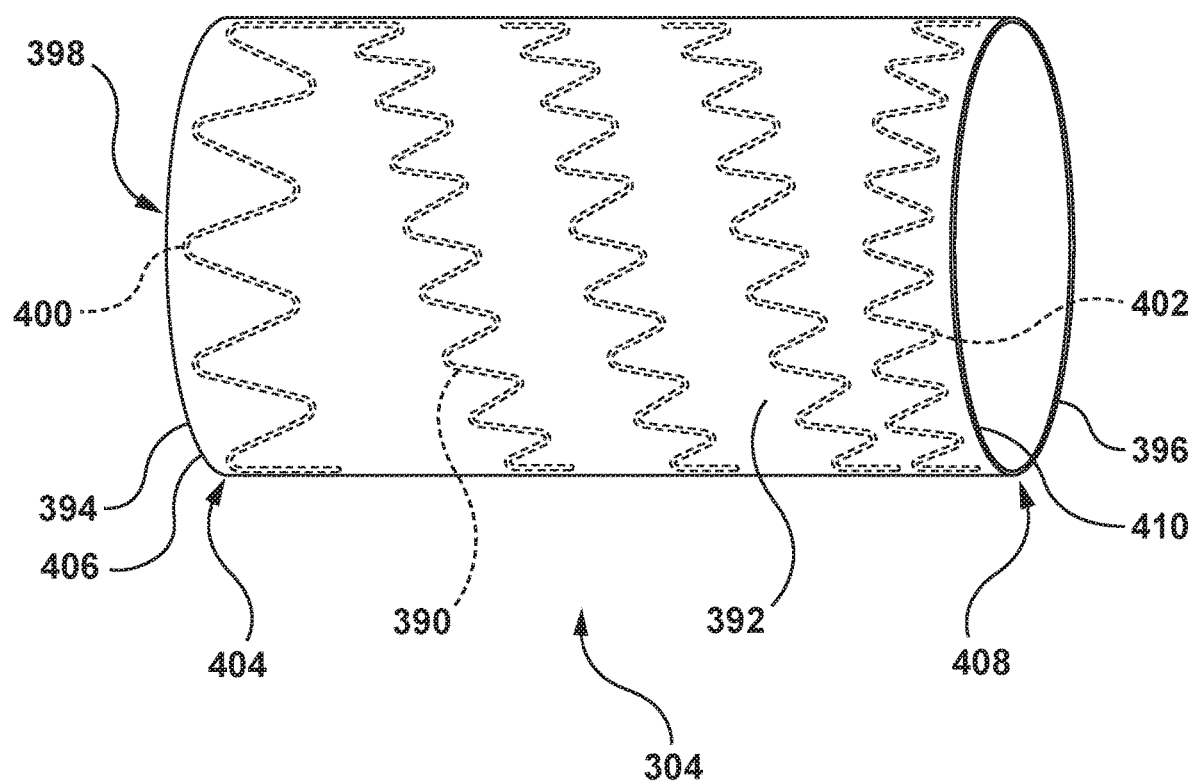
FIG. 12 is a close up perspective illustration of an embodiment of a second prosthesis of the dissection prosthesis system of FIG. 3 in a radially expanded deployed configuration.

FIG. 12 illustrates an embodiment of second prosthesis 304. Second prosthesis 304 is of a generally tubular configuration including a proximal end 294 and a distal end 396, and defines a lumen 398 therein. Second prosthesis 304 includes a stent 390 coupled to graft material 392. Second prosthesis 304 is radially expandable from a radially compressed delivery configuration (FIG. 18) to a radially expanded deployed configuration, as shown in FIGS. 4-5, 12, and FIG. 19-21. Second prosthesis 304 is configured to be disposed within lumen 320 of first prosthesis 302 at the site of tear 514 of aortic dissection 502, as shown in FIG. 5, to close off tear 514 such that blood does not flow through tear 514 into the false lumen. Second prosthesis 304 is further configured such that second prosthesis 304, when disposed within lumen 320 of first stent 302 in the radially expanded deployed configuration, includes a fifth outward radial force OF5. Second prosthesis 304 may be self-expanding or balloon expandable, preferably self-expanding.

In an embodiment, stent 390 of second prosthesis 304 is a stent structure as is known in the art. Stent 390 includes a proximal end 400 and a distal end 402, as shown in FIG. 12. Stent 390 is radially expandable from a radially compressed delivery configuration (FIG. 18) to a radially expanded deployed configuration, as shown in FIGS. 4-5, 12, and 19-21. Stent 390 of second prosthesis 304 is configured to provide a flexible, conformable stent, which expands uniformly and provides fifth outward radial force OF5, as described previously. Stent 390 may be formed, for example, and not by way of limitation, of a nickel-titanium alloy, Nitinol, a nickel-cobalt-chromium-molybdenum alloy (MP35N), stainless steel, high spring temper steel, or any other metal or composite having elastic properties to permit extension and recoil suitable for purposes of the present disclosure.

Graft material 392 of second prosthesis 304 is a graft material, as is known in the art. Graft material 392 is of a generally tubular configuration and includes a proximal edge portion 404, a proximal edge 406, a distal edge portion 408, and a distal edge 410 as shown in FIG. 12. In an embodiment, graft material 392 is disposed about an outer surface of stent 390. However, graft material may instead be coupled to an inner surface of stent 390. Graft material 392 folds or compresses with radial compression of stent 390 for delivery, and unfolds or expands with radial expansion of stent 390 for deployment at the treatment site. In the embodiment with graft material 392 disposed about the outside surface of stent 390, graft material 392 is configured to cover tear 514 of aortic dissection 502. Graft material 392 is further configured to shield stent 390 from direct contact with inner wall 506 of aorta 500, thereby reducing the possibility of damage to inner wall 506. Graft material 392 of second prosthesis 304 may be formed, for example, and not by way of limitation, of woven polyester such as polyethylene terephthalate, polytetrafluoroethylene (PTFE), electrospun polyethelene (PE), or any other material suitable for purposes of the present disclosure. Graft material 392 of second prosthesis 304 may be coupled to stent 390 in a manner such as, but not limited to sutures, adhesives, or other methods suitable for the purposes disclosed herein.

While second prosthesis 304 is shown in FIG. 12 with stent 390 as a helical structure, it is not meant to limit the design, and other configurations including ring configurations may be utilized.

Figure 13:
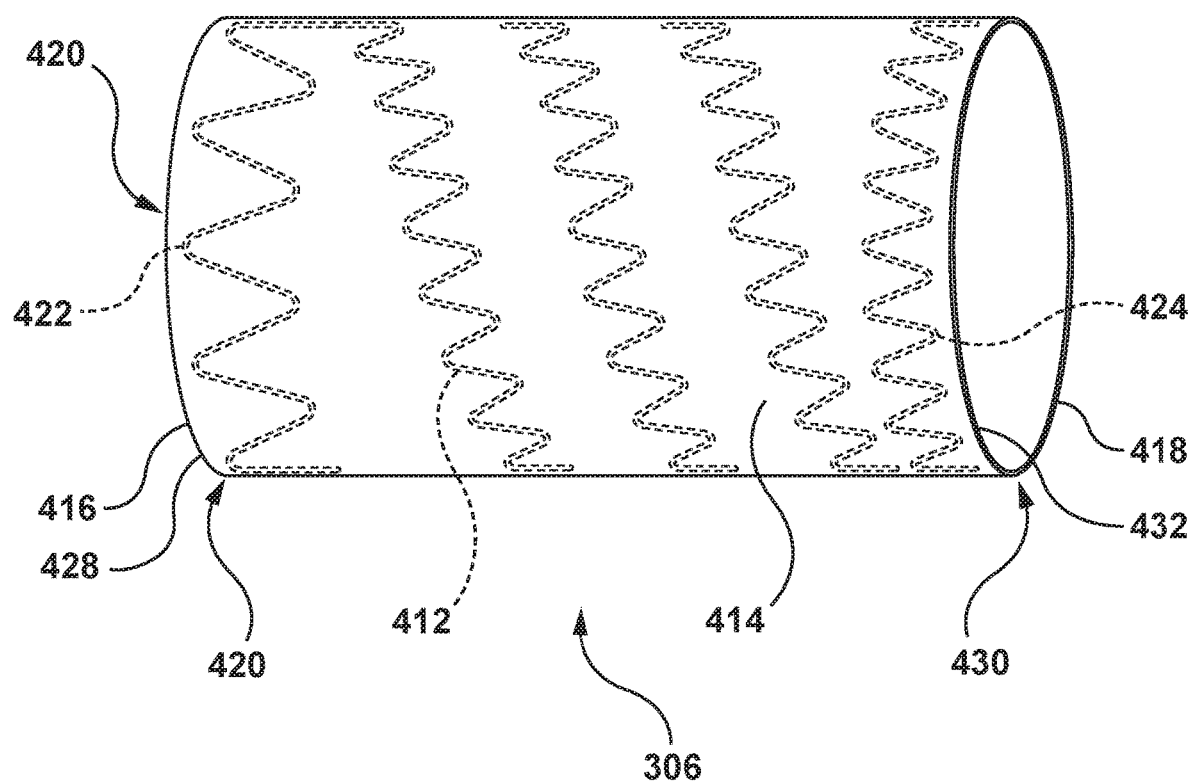
FIG. 13 is a close up perspective illustration of an embodiment of a third prosthesis of the dissection prosthesis system of FIG. 3 in a radially expanded deployed configuration.
Figure 19:
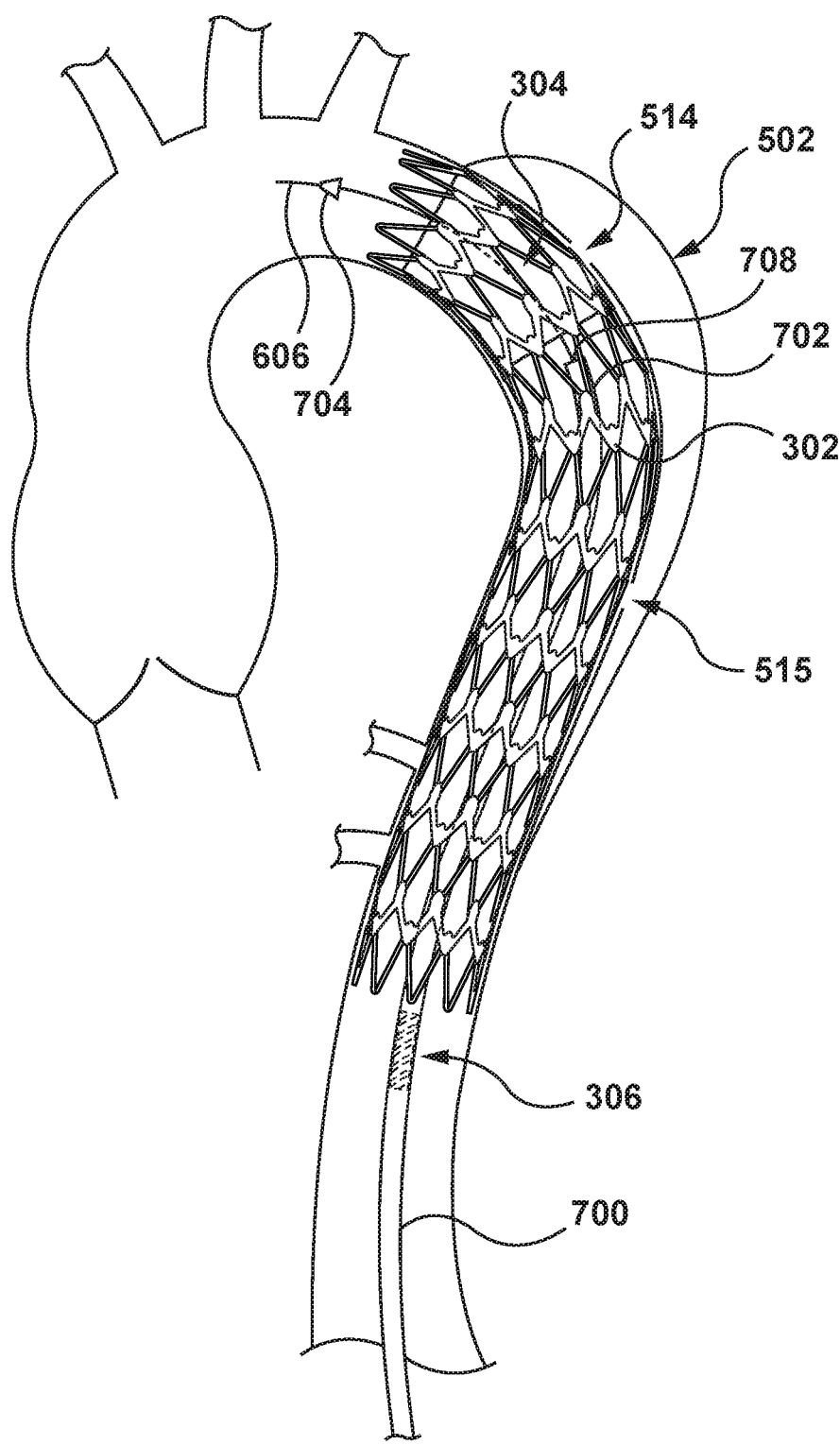
Figure 20:
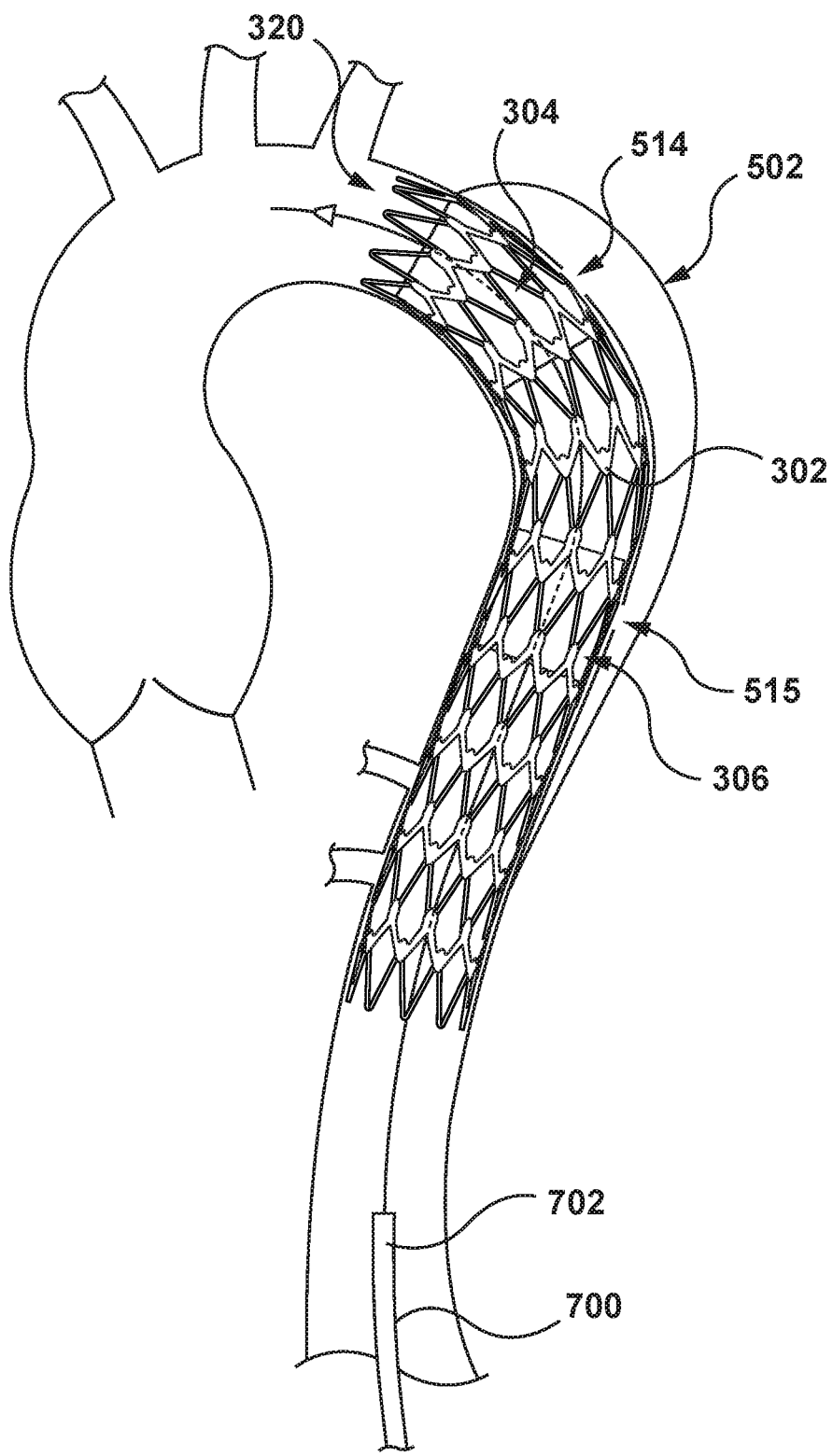
Figure 21:
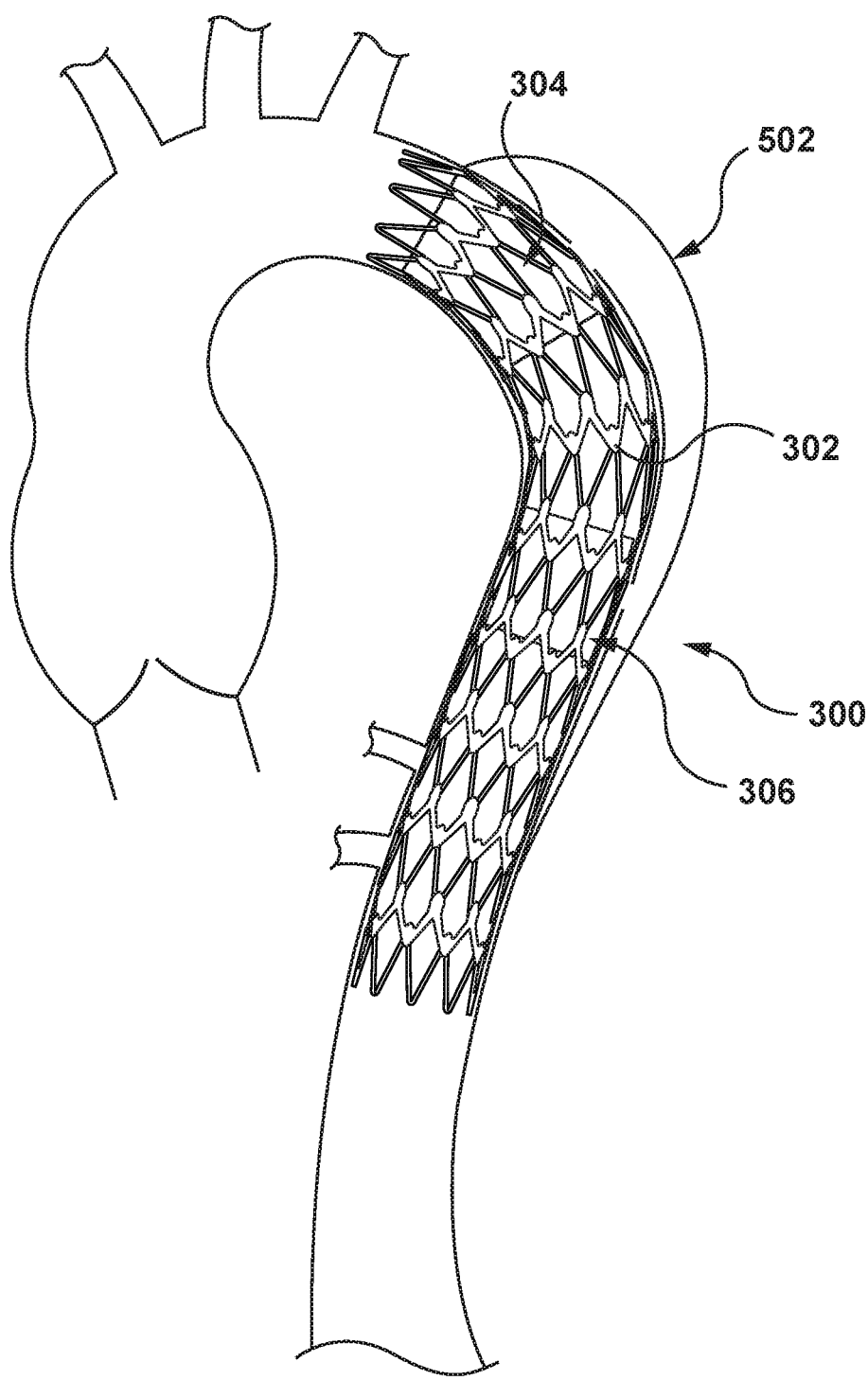

FIG. 13 illustrates an embodiment of a third prosthesis 306. Third prosthesis 306 is of a generally tubular configuration including a proximal end 416 and a distal end 414, and defines a lumen 420 therein. Third prosthesis 306 includes a stent 412 coupled to graft material 414. Third prosthesis 306 is radially expandable from a radially compressed delivery configuration (FIG. 18) to a radially expanded deployed configuration, as shown in FIG. 4-5, 13, and FIG. 19-21. In an embodiment, third prosthesis 306 is configured to be disposed within lumen 320 of first prosthesis 302 at a location different from second prosthesis 304, as shown in FIG. 5. For example, and not by way of limitation, third prosthesis 306 may be disposed at a location of a second tear 515 (FIGS. 20-21). In another embodiment, third prosthesis 306 may be disposed within a distal potion of first prosthesis 302 to prevent distal progression of dissection 502. Third prosthesis 306 includes a sixth outward radial force OF6. Third prosthesis 306 may be self-expanding or balloon expandable, preferably self-expanding.

In an embodiment, stent 412 of third prosthesis 306 is a stent structure as is known in the art, and as shown in FIG. 13. Stent 412 includes a proximal end 422 and a distal end 424. Stent 412 is radially expandable from a radially compressed delivery configuration (FIG. 18-19) to a radially expanded deployed configuration, as shown in FIG. 13. Stent 412 of third prosthesis 306 is configured to provide a flexible, conformable stent, which expands uniformly and provides sixth outward radial force OF6 as described previously. Stent 412 may be formed, for example, and not by way of limitation, of a nickel-titanium alloy, Nitinol, a nickel-cobalt-chromium-molybdenum alloy (MP35N), stainless steel, high spring temper steel, or any other metal or composite having elastic properties to permit extension and recoil suitable for purposes of the present disclosure.

Graft material 414 of third prosthesis 306 is a graft material, as is known in the art. Graft material 414 is of a generally tubular configuration and includes a proximal edge portion 426, a proximal edge 428, a distal edge portion 430, and a distal edge 432 as shown in FIG. 13. In an embodiment, graft material 414 is disposed about an outer surface of stent 412. However, graft material 414 may be coupled to an inner surface of stent 412. Graft materials 414 folds or compresses with radial compression of stent 412 for delivery, and unfolds or expands with radial expansion of stent 412 for deployment at the treatment site. In the embodiment where graft material 414 is disposed about an outside surface of stent 412, graft material 414 is configured to cover a tear, such as second tear 515 of aortic dissection 502, as shown in FIG. 19. Graft material 414 is further configured to shield stent 412 from direct contact with inner wall 506 of aorta 500, thereby reducing the possibility of damage to inner wall 506. Graft material 414 of third prosthesis 306 may be formed, for example, and not by way of limitation, of woven polyester such as polyethylene terephthalate, polytetrafluoroethylene (PTFE), electrospun polyethelene (PE), or any other material suitable for purposes of the present disclosure. Graft material 414 of third prosthesis 306 may be coupled to stent 412 in a manner such as, but not limited to sutures, adhesives, or other methods suitable for the purposes disclosed herein.

While third prosthesis 306 is shown in FIG. 13 with stent 412 as a helical structure, it is not meant to limit the design, and other configurations including ring configurations may be utilized.

While dissection prosthesis system 300 is shown in FIGS. 3-13 as including third prosthesis 306, this is not meant to limit the design, and additional or fewer prostheses may be utilized.

Figure 14:
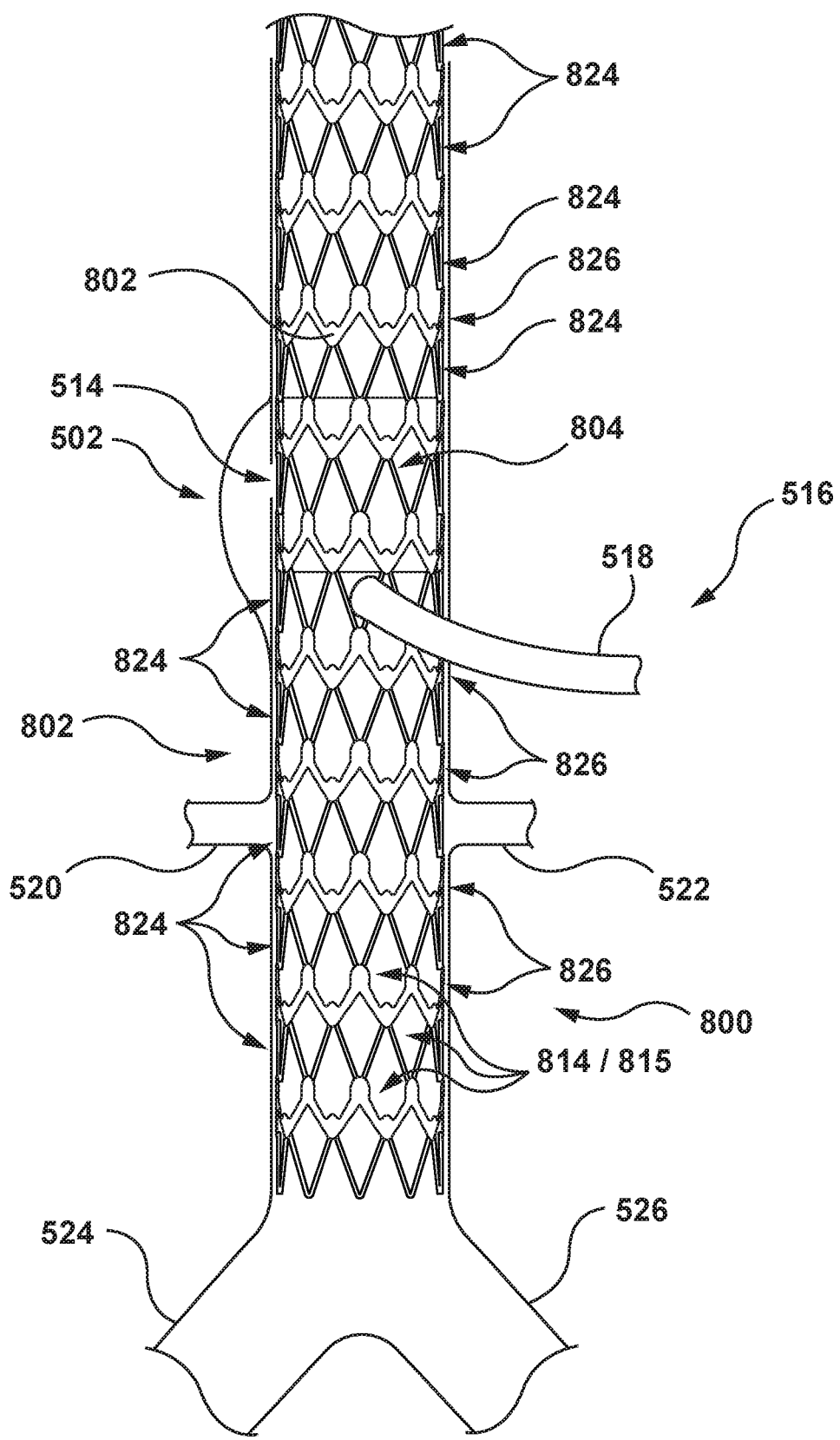
FIG. 14 is a cutaway side illustration of an embodiment of a dissection prosthesis system deployed within an abdominal aorta.

As explained above, while dissection prosthesis system 300 is shown in FIG. 5 deployed at the site of an aortic dissection of the descending aorta, this is not meant to limit the design and other configurations and deployment locations may be utilized. For example, and not by way of limitation, FIG. 14 illustrates an embodiment of a dissection prosthesis system 800 disposed in the abdominal aorta. Dissection prosthesis system 800 includes a first prosthesis 802 similar to first prosthesis 302. As described previously with respect to first prosthesis 302, first prosthesis 802 includes a proximal stent 822, a plurality of stent rings 824 with openings 814, a plurality of graft material bands 826 with openings 815, and a distal stent 828. Dissection prosthesis system 800 further includes a second prosthesis 804 similar to second prosthesis 304 of dissection prosthesis system 300. Therefore, specific details of first prosthesis 802 and second prosthesis 804 are not repeated here. Dissection prosthesis system 800 is configured for deployment in an abdominal aorta 516 to seal a tear 514 of an aortic dissection 502. More specifically, first prosthesis 802 with second prosthesis 804 disposed therein covers tear 514 to prevent blood flow into aortic dissection 502. Further, due to openings 814 in stent rings 824 and band openings 815 through graft material bands 826, dissection prosthesis system 800 maintains blood flow to the superior mesenteric artery (SMA) 518, left renal artery 520, and right renal artery 522.

Additional or fewer stent rings 824 and graft material bands 826 may be utilized depending on the length of first prosthesis 802 desired. For example, and not by way of limitation, first prosthesis 802 may extend from distal of the left subclavian artery 536 (FIG. 5) to the left and right iliac arteries 524, 526 (FIG. 14). Further, additional prostheses, similar to second prosthesis 804, may be utilized to cover additional tears into dissection 502 or into other dissections in the area.

Figure 15:
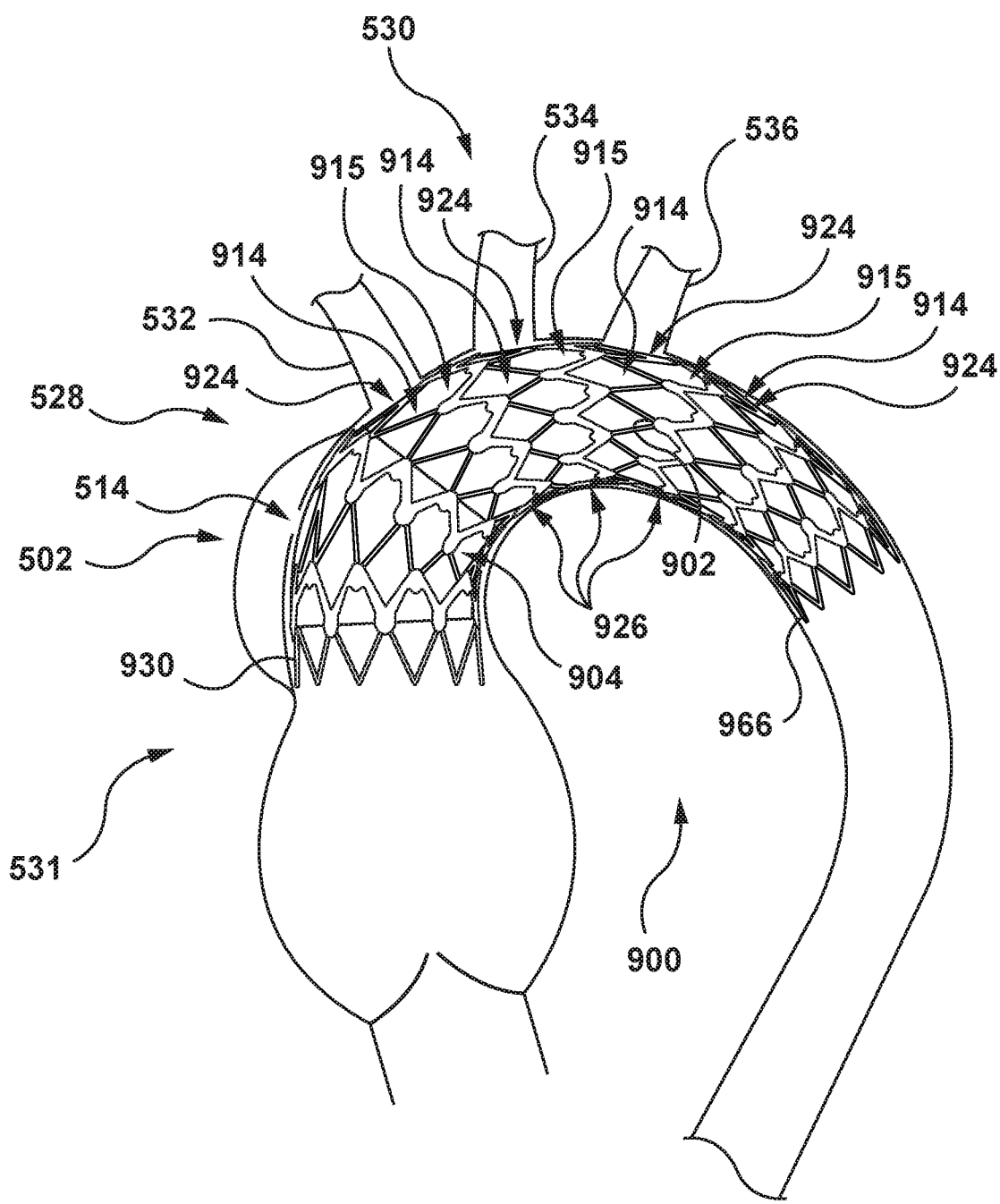
FIG. 15 is a cutaway side illustration of an embodiment of a dissection prosthesis system deployed within an ascending aorta and aortic arch.

FIG. 15 illustrates an embodiment of a dissection prosthesis system 900 disposed in the aortic arch. Dissection prosthesis system 900 includes a first prosthesis 902 similar first prosthesis 302 and a second prosthesis 904 similar to second prosthesis 304. As described previously with respect to first prosthesis 302, first prosthesis 902 includes a proximal stent ring 930, stent rings 924, graft material bands 926, and a distal stent ring 966. Therefore, details of first prosthesis 902 and second prosthesis 904 are not repeated here. Dissection prosthesis system 900 is configured for deployment in an ascending aorta 528 and over the aortic arch 530 to seal a tear 514 of an aortic dissection 502. More specifically, first prosthesis 902 with second prosthesis 904 disposed therein, covers tear 514 to prevent blood flow into aortic dissection 502. Further, due to openings 914 in stent rings 924 and band openings 915 through graft material bands 926, dissection prosthesis system 900 maintains blood flow to the innominate artery 532, the left carotid artery 534, and the left subclavian artery 536. In such an embodiment, second prosthesis 904 may extend the entire length from just distal of the aortic sinuses 531 to just proximal of the innominate artery 532.

Additional or fewer stent rings 924 and graft material bands 926 may be utilized depending on the length of first prosthesis 902 desired. For example, and not by way of limitation, first prosthesis 902 may extend further distally in the descending aorta. Further, additional prostheses, similar to second prosthesis 904, may be utilized to cover additional tears into dissection 502 or into other dissections, provided that such prostheses do not cover the arteries of the aortic arch. For example, and not by way of limitation, the dissection 502 may extend distal of aortic arch 530, and an additional prosthesis 904 may cover a second tear (not shown) distal of the arteries of the aortic arch.

Figure 16:
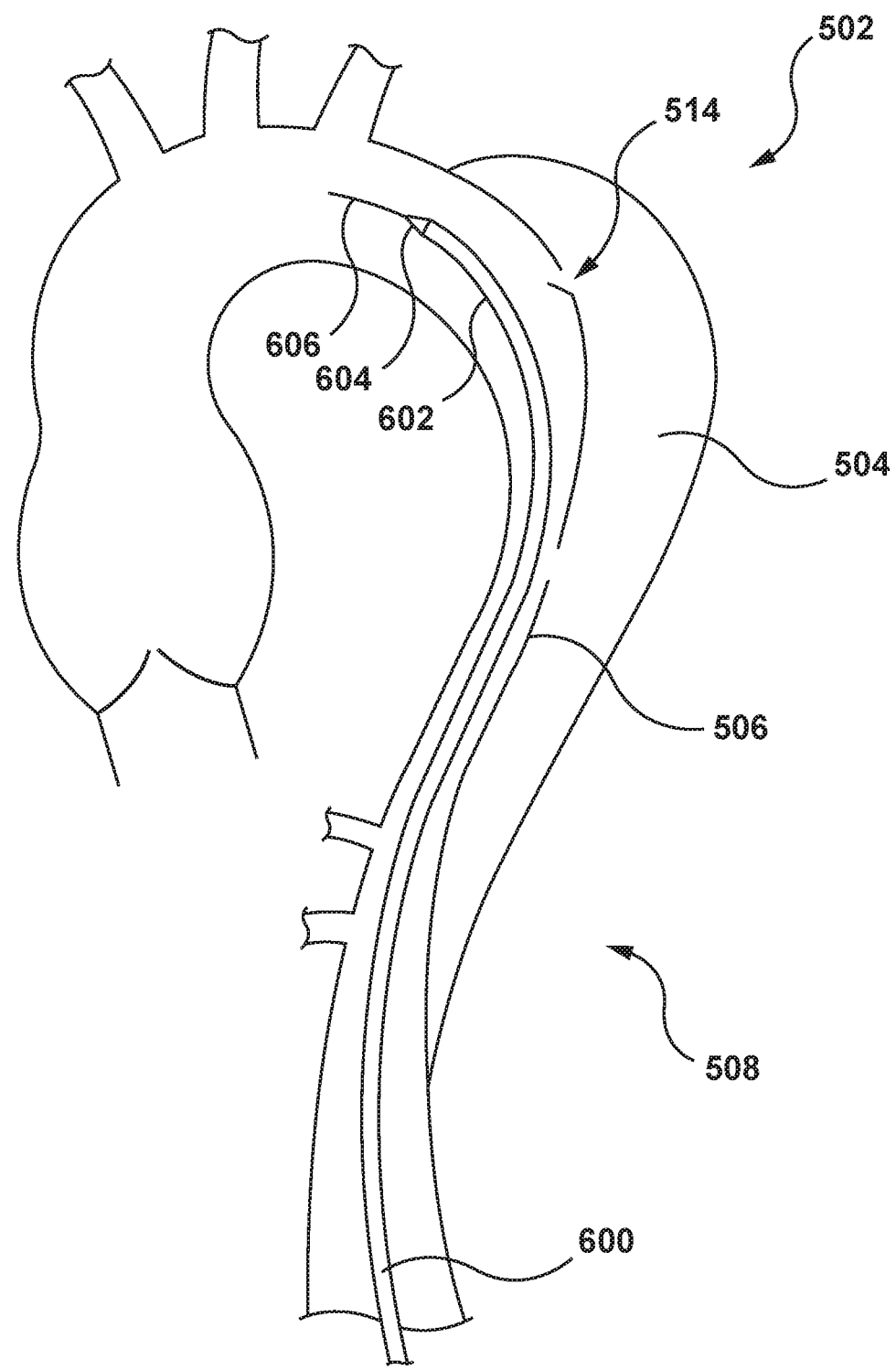
FIGS. 16-21 are simplified illustrations of some steps of an embodiment of a method of delivering and deploying a dissection prosthesis system at a treatment site of an aortic dissection.

FIGS. 16-21 show schematically an embodiment of a method of treating an aortic dissection 502 with a dissection prosthesis system 300. Using established percutaneous transcatheter procedures, a delivery device 600 including first prosthesis 302 disposed therein in a radially compressed delivery configuration is introduced into a patient's vasculature and positioned at a treatment site of an aortic dissection 502, as shown in FIG. 16. In the embodiment shown, aortic dissection 502 is located in descending aorta 508, and includes a tear 514 in an inner wall 506, wherein blood may flow and inflate a false lumen 504. Delivery device 600 may include various features and components as are known in the art, including a sheath shaft 602, a distal tip 604, and a guidewire 606, as shown in FIG. 16. Other details regarding delivery device 600 are not described herein, as various additional features are known to those skilled in the art. Although the method is described herein using dissection prosthesis system 300, it will be apparent to one of ordinary skill that methods described herein may utilize a dissection prosthesis system according to any embodiment described herein. Delivery device 600 and/or first prosthesis 302 of dissection prosthesis system 300 may also include, for example, radiopaque markers such that clinician may determine when delivery device 600 and/or first prosthesis 302 is in the proper location for deployment.

Figure 17:
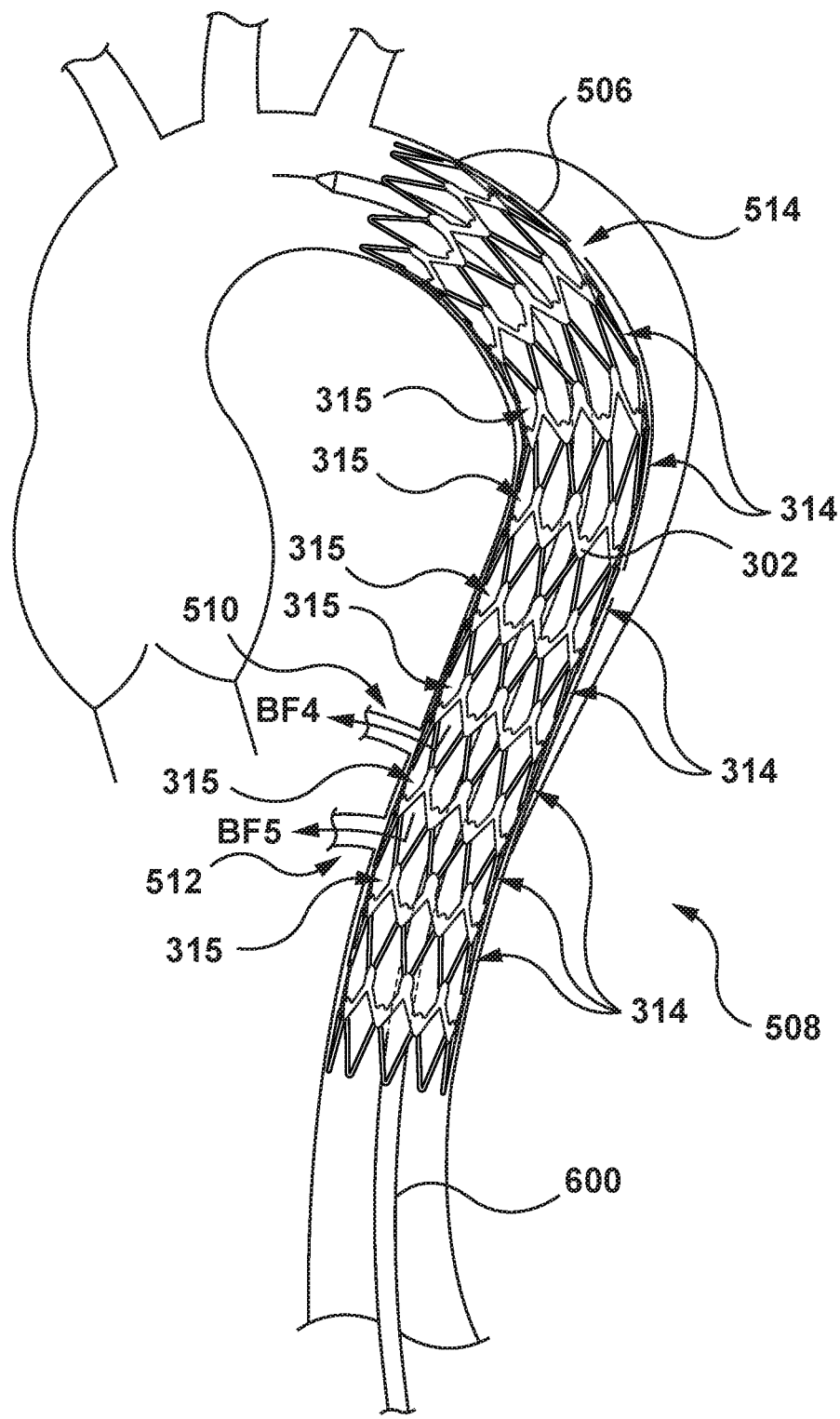

With delivery device 600 at the desired location, delivery device 600 is manipulated to release first prosthesis 302 from delivery device 600. For example, and not by way of limitation, first prosthesis 302 may be self-expanding, and first prosthesis 302 may be deployed from delivery device 600 by retracting sheath 602 to uncover first prosthesis 302 and enable first prosthesis 302 to self-expand. Thus, first prosthesis 302 transitions from the radially compressed delivery configuration to a radially expanded deployed configuration. Upon expansion thereof, an outer surface of first prosthesis 302 engages an inner wall 506 of descending aorta 508, as shown in FIG. 17. First prosthesis 302, when in the radially expanded deployed configuration within descending aorta 508, is disposed such that first prosthesis 302 extends distally and proximally of tear 514, and openings 314, 315 enable fourth blood flow BF4 and fifth blood flow BF5 to branch and ancillary arteries, such as, but not limited to intercostal arteries 510 and subcostal arteries 512, as shown in FIG. 17.

Figure 18:
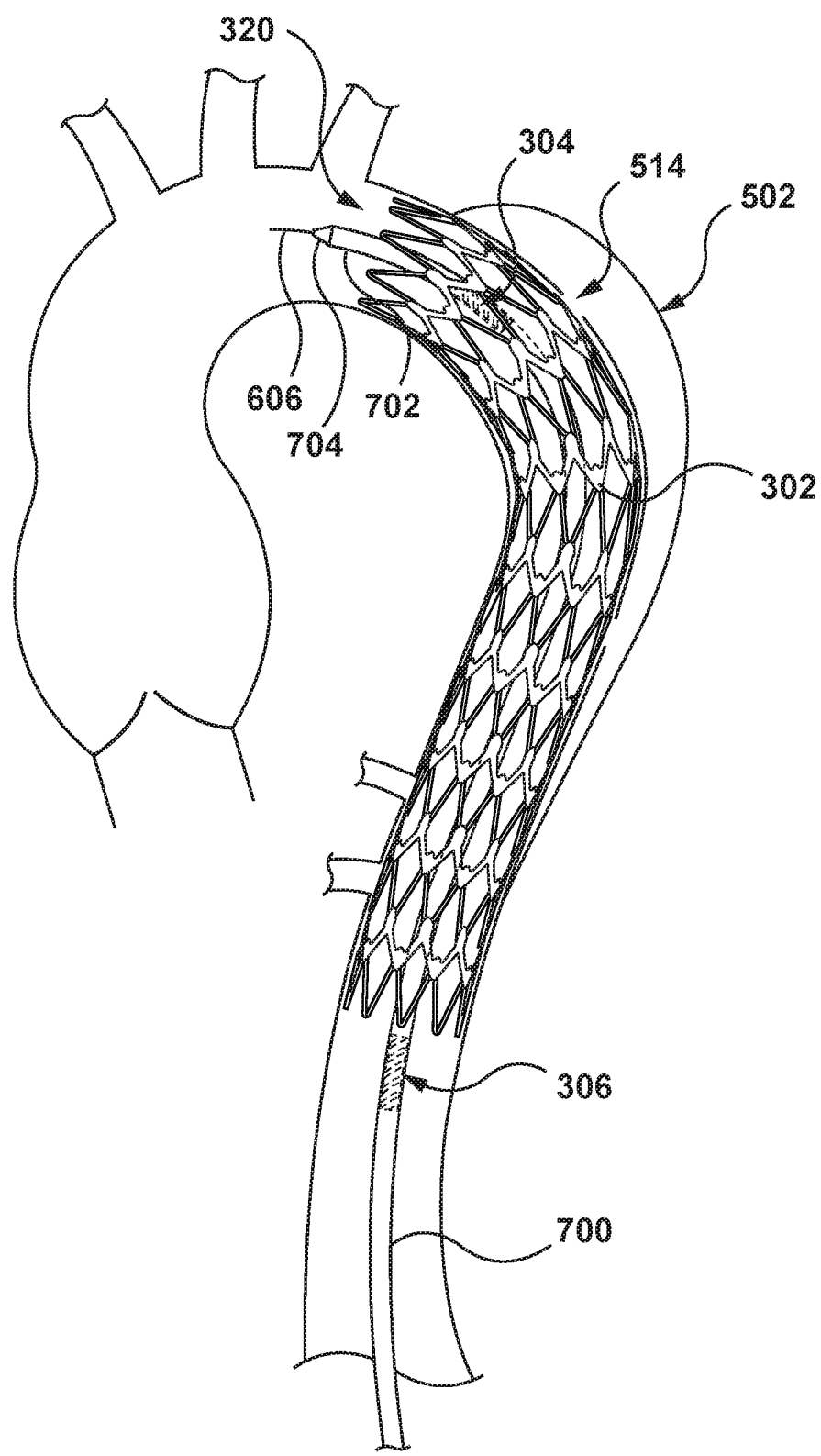

In an embodiment, delivery device 600 is removed from the body (not shown) and a second delivery device 700 is advanced distally within lumen 320 of first prosthesis 302 to the site of tear 514 of aortic dissection 502, as shown in FIG. 18. Second delivery device 700 includes second prosthesis 304 disposed therein in a radially compressed delivery configuration. Second delivery device 700, and/or second prosthesis 304, may include, for example, radiopaque markers such that a clinician may determine when second delivery device 700 and/or second prosthesis 304 is in the proper location for deployment. Second delivery device 700 may include known features of delivery devices, such as, but not limited to, a sheath 702, an inner shaft 708 (FIG. 19) including a guidewire lumen, and a distal tip 704. Second delivery device 700 may be advanced over guidewire 606. In an embodiment, third prosthesis 306 may be disposed within second delivery device 700 in a radially compressed delivery configuration with second prosthesis 304. In another embodiment (not shown), second prosthesis 304 may be disposed within delivery device 600 in a radially compressed delivery configuration, together with first prosthesis 302. In such an embodiment, delivery device 600 is manipulated to locate second prosthesis 304 at the desired location.

With second delivery device 700 at the desired location, second delivery device 700 is manipulated to release second prosthesis 304 from second delivery device 700, and second prosthesis 304 transitions from the radially compressed delivery configuration to a radially expanded deployed configuration. For example, and not by way of limitation sheath 702 of second delivery device 700 may be retracted to expose second prosthesis 304, thereby enabling second prosthesis 304 to radially expand. Upon expansion thereof, an outer surface of second prosthesis 304 engages an inner surface of first prosthesis 302 at the site of tear 514 of aortic dissection 502, as shown in FIG. 19. Second prosthesis 304, when in the radially expanded deployed configuration within first prosthesis 302 is disposed such that second prosthesis 304 covers tear 514 to prevent blood flow from the aorta, through tear 514, and into the false lumen.

In an embodiment, after second prosthesis 304 is deployed, second delivery device 700 may be manipulated to locate third prosthesis 306 at a desired location such as covering a second tear 515 of dissection 502. In a non-limiting example, sheath 702 may be moved distally to distal tip 704 to close second delivery device 700 prior to being moved. In another non-limiting example, second delivery device 700 may be removed from the body and a third delivery device (not shown) with third prosthesis 306 disposed therein, may be advanced or retracted to the desired location. Second delivery device 700 and/or third prosthesis 306 may also include, for example, radiopaque markers such that clinician may determine when second delivery device 700 and/or third prosthesis 306 is in the proper location for deployment. In the embodiment shown, third prosthesis 306 is located at the location of a second tear 515 of aortic dissection 502, distal of tear 514. However, third prosthesis 306 and additional prostheses may be located anywhere a clinician desires to cover additional tears and/or additional support. With second delivery device 700 at the desired location, second delivery device 700 is manipulated to release third prosthesis 306 from second delivery device 700, and third prosthesis 306 transitions from the radially compressed delivery configuration to a radially expanded deployed configuration, as shown in FIG. 20. For example, and not by way of limitation sheath 702 of second delivery device 700 may be retracted to expose third prosthesis 306, thereby enabling third prosthesis 306 to radially expand. In an embodiment, upon expansion thereof, an outer surface of third prosthesis 306 engages the inner surface of first prosthesis 302 distal of second prosthesis 304, as shown in FIG. 20. In an embodiment, third prosthesis 306 is configured such that third prosthesis 306 is disposed within lumen 320 of first prosthesis 302 at the location of second tear 515 of aortic dissection 502. Alternatively, third prosthesis 306 may be deployed within a distal potion of first prosthesis 302 to assist in preventing distal progression of dissection 502.

Once dissection prosthesis system 300 is fully deployed and in the radially expanded deployed configuration, second delivery device 700 may be retracted and removed from the patient's vasculature using established procedures, leaving dissection prosthesis system 300 at aortic dissection 502 treatment site, as shown in FIG. 21.

While intercostal arteries 510 and subcostal arteries 512 are each shown in FIGS. 16-21 as a single vessel, this is for illustrative purposes only and intercostal arteries 510 and subcostal arteries 512 each represent a plurality of arteries. Further, additional branch or ancillary arteries may also emanate from the target vessel, but are not shown for clarity of the drawings.

While the method of FIGS. 16-21 show an embodiment of dissection prosthesis system 300 deployed within the descending aorta, those skilled in the art will understand that the method described with FIGS. 16-21 would also apply to other embodiments at other locations within the aorta, such as the abdominal aorta with dissection prostheses systems 800 of FIG. 14, the ascending aorta and aortic arch with dissection prosthesis system 900 of FIG. 15, or other locations.

While only some embodiments have been described herein, it should be understood that it has been presented by way of illustration and example only, and not limitation. Various changes in form and detail can be made therein without departing from the spirit and scope of the invention, and each feature of the embodiments discussed herein, and of each reference cited herein, can be used in combination with the features of any other embodiment. All patents and publications discussed herein are incorporated by reference herein in their entirety.

What is claimed is:

1. A dissection prosthesis system comprising:
  a first prosthesis having a generally tubular shape, a radially compressed delivery configuration and a radially expanded deployed configuration, the first prosthesis comprising;
    a plurality of stent rings, each of the plurality of stent rings having a proximal end and a distal end, wherein each of the plurality of stent rings includes a plurality of openings between the respective stent ring proximal and distal ends thereof; and
    a plurality of graft material bands, each graft material band having a proximal edge portion and a distal edge portion and a plurality of band openings between the proximal edge portion and the distal edge portion;
  wherein each one of the plurality of graft material bands is disposed between and couples together a respective adjacent pair of the plurality of stent rings such that each graft material proximal edge portion is attached to a respective stent ring distal end and each graft material distal end portion is attached to a respective proximal end of an adjacent stent ring; and
  wherein the plurality of openings in the stent rings and the plurality of band openings in the graft material bands enable fluid flow from a lumen of the prosthesis through the openings and band openings
  wherein the graft material bands have a zig-zag shape in a longitudinal direction, wherein the plurality of band openings are formed between struts of the zig-zag shape.

2. The prosthesis of claim 1, wherein at least a pair of adjacent stent rings of the plurality of stent rings are coupled to each other only by graft material bands.

3. The prosthesis of claim 1, wherein the material bands are disposed on an outer surface of the stent rings.

4. The prosthesis of claim 1, further comprising a proximal stent ring disposed at the proximal end of the prosthesis, wherein the proximal stent ring is covered by a graft material.

5. The prosthesis of claim 1, further comprising a distal stent ring disposed at the distal end of the prosthesis, wherein the distal stent ring is covered by a graft material.

6. The prosthesis of claim 1, further comprising a distal stent ring disposed at a distal end of the prosthesis, wherein the plurality of stent rings each have a radially outward force that is greater than a radially outward force of the distal stent ring.

7. The dissection prosthesis of claim 1, wherein the material of the plurality of graft material bands is a woven polyester material.

8. A dissection prosthesis system comprising:
  a first prosthesis having a generally tubular shape, a radially compressed delivery configuration and a radially expanded deployed configuration, the first prosthesis comprising;
    a plurality of stent rings, each of the plurality of stent rings having a proximal end and a distal end, wherein each of the plurality of stent rings includes a plurality of openings between the respective stent ring proximal and distal ends thereof; and
    a plurality of graft material bands, each graft material band having a proximal edge portion and a distal edge portion and a plurality of band openings between the proximal edge portion and the distal edge portion, wherein each of the plurality of graft material bands includes a plurality of proximal landing points, a plurality of distal landing points, and a plurality of connecting portions configured such that each connecting portion is disposed between and couples one of the plurality of proximal landing points and one of the plurality of distal landing points, wherein the plurality of band openings of each of the plurality of graft material bands is formed between the respective connecting portions, proximal landing points, and distal landing points;
  wherein each one of the plurality of graft material bands is disposed between and couples together a respective adjacent pair of the plurality of stent rings such that each graft material proximal edge portion is attached to a respective stent ring distal end and each graft material distal end portion is attached to a respective proximal end of an adjacent stent ring; and wherein the plurality of openings in the stent rings and the plurality of band openings in the graft material bands enable fluid flow from a lumen of the prosthesis through the openings and band openings.

9. The dissection prosthesis system of claim 8, further comprising:

a second prosthesis having a generally tubular shape, a radially compressed delivery configuration and a radially expanded deployed configuration, the second prosthesis comprising a stent and a graft material coupled to the stent;

wherein the second prosthesis is configured to be disposed within the lumen of the first prosthesis.

10. The dissection prosthesis system of claim 9, wherein a first outward radial force of the first prosthesis in the radially expanded deployed configuration is less than a second outward radial force of the second prosthesis in the radially expanded deployed configuration.

11. The dissection prosthesis system of claim 9, wherein the second prosthesis comprises a plurality of stents.

12. The dissection prosthesis system of claim 9, further comprising a third prosthesis having a generally tubular shape, a radially compressed delivery configuration and a radially expanded deployed configuration, the third prosthesis comprising a stent and a graft material coupled to the stent, wherein the third prosthesis is configured to be disposed within the lumen of the first prosthesis at a location different from the second prosthesis.

13. The dissection prosthesis system of claim 8, wherein the plurality of graft material bands are made from a woven polyester material.

14. The dissection prosthesis system of claim 8, wherein each of plurality of stent rings includes a plurality of proximal apices and a plurality of distal apices, and wherein the distal apices of first stent ring of the plurality of stent rings are coupled to respective proximal landing points of one of the plurality of graft material bands, and the proximal apices of a second stent ring of the plurality of stent rings adjacent the first stent ring are coupled to respective distal landing points of the one of the plurality of graft material bands.

* * * * *